United States Patent
Sugawara et al.

(10) Patent No.: US 6,720,449 B2
(45) Date of Patent: Apr. 13, 2004

(54) PROCESS FOR PREPARING OPTICALLY ACTIVE AMINO ACID DERIVATIVES

(75) Inventors: Masanobu Sugawara, Chiba (JP); Akio Fujii, Hyogo (JP); Kazumi Okuro, Hyogo (JP); Yasuhiro Saka, Hyogo (JP); Nobuo Nagashima, Hyogo (JP); Kenji Inoue, Hyogo (JP); Toshihiro Takeda, Hyogo (JP); Koichi Kinoshita, Hyogo (JP); Tadashi Moroshima, Hyogo (JP); Yoshihide Fuse, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 33 days.

(21) Appl. No.: 09/926,346
(22) PCT Filed: Feb. 16, 2001
(86) PCT No.: PCT/JP01/01132
  § 371 (c)(1),
  (2), (4) Date: Feb. 5, 2002
(87) PCT Pub. No.: WO01/60795
  PCT Pub. Date: Aug. 23, 2001

(65) Prior Publication Data
US 2003/0032814 A1 Feb. 13, 2003

(30) Foreign Application Priority Data
Feb. 17, 2000 (JP) .................................. P2000-039415
Nov. 1, 2000 (JP) .................................. P2000-334391

(51) Int. Cl.⁷ ...................... C07D 203/08; C07C 227/04
(52) U.S. Cl. ........................................ 562/496; 548/954
(58) Field of Search ........................... 562/496; 548/954

(56) References Cited

FOREIGN PATENT DOCUMENTS

| | | |
|---|---|---|
| GB | 847205 | 9/1960 |
| JP | 35-5474 | 5/1960 |
| JP | 35-8315 | 7/1960 |
| JP | 45-17420 | 6/1970 |
| JP | 50-49227 | 5/1975 |
| JP | 57-146751 | 9/1982 |
| JP | 7-138281 | 5/1995 |
| JP | 11-171860 | 6/1999 |
| WO | WO82/04043 | 11/1982 |

OTHER PUBLICATIONS

Church, et al, J. Chem. Soc., Chem. Commmun. 1994, 943–944.*
Dauban, et al, Tetrahedron Letters, 39, 1998, 5739–5742.*
P. Müller et al.; Can. J. Chem. 76, vol. 76, pp. 738–750, 1998. See PCT search report.
P. Müller et al.; Journal of Physical Organic Chemistry, vol. 9, pp. 341–347, 1996. See PCT search report.

* cited by examiner

Primary Examiner—Joseph K. McKane
Assistant Examiner—Andrea D. Small
(74) Attorney, Agent, or Firm—Westerman, Hattori, Daniels & Adrian, LLP

(57) ABSTRACT

An optically active amino acid derivative is produced by N-protecting an optically active 3-haloalanine derivative followed by cyclization, or cyclizing this derivative followed by N-protection to thereby give an optically active N-protected-aziridine-2-carboxylic acid derivative which is protected by a benzenesulfonyl group substituted by nitro at the 2- and/or 4-positions and then treating this product with an organic metal reagent, or by N-protecting an optically active 3-haloalanine derivative to thereby give N-protected-aziridine-2-carboxylic acid which is protected by a benzenesulfonyl group substituted by nitro at the 2- and/or 4-positions and then treating this product with an organic metal reagent.

According to this process, natural and unnatural optically active amino acids can be produced from inexpensive materials by using simple procedures.

9 Claims, 1 Drawing Sheet

PROCESS FOR PREPARING OPTICALLY ACTIVE AMINO ACID DERIVATIVES

TECHNICAL FIELD

This invention relates to processes for producing optically active amino acid derivatives, optically active N-protected-aziridine-2-carboxylic acid and optically active aziridine-2-carboxylic acid derivatives, which are useful as intermediates of drugs and pesticides, physiologically active substances, etc., and salts thereof.

BACKGROUND ART

There have been known a great number of optically active natural or unnatural amino acid derivatives which are useful as intermediates of drugs and pesticides, physiologically active substances, etc. It is still an important problem to develop an efficient process for producing these derivatives. As noteworthy processes, there have been reported several processes of activating the OH-group at the β-position of optically active serine and then reacting with a nucleophile or an electrophile.

Examples of these processes are as follows:

(1) a process wherein an optically active N-tosyl-aziridine-2-carboxylic acid derivative is reacted with lithium acetylide of trimethylsilyl acetylene (Tetrahedron Lett. vol. 36, 151 (1995));

(2) a process wherein an optically active N-protected-3-iodo-alanyl ester is substituted at the 3-position by reacting with a nucleophile (Tetrahedron, vol. 41, 1833 (1985));

(3) a process wherein an optically active N-protected-3-iodo-alanyl ester is converted into an organic zinc compound and then reacted with an electrophile (J.O.C., vol. 57, 3397 (1992));

(4) a process wherein a β-lactam derivative or a sulfamidate derivative is produced from a serine derivative and then reacted with a nucleophile (J. Am. Chem. Soc., vol. 107, 7105 (1985)); and (5) a process wherein an optically active N-protected-aziridine-2-carboxylic acid ester is synthesized from a serine derivative and then reacted with an organic copper reagent (JP-A-7-252202; the term "JP-A" as used herein means an "unexamined published Japanese patent application"), etc.

In addition, there has been known a process for producing aziridine-2-carboxylic acid by treating a 3-haloalanine or its ester or a mineral acid salt thereof with an alkali metal or alkaline earth metal hydroxide or aqueous ammonia in water or an aqueous organic solvent (JP-B-60-39357; the term "JP-B" as used herein means an "examined Japanese patent publication").

Among the processes of activating the OH-group at the β-position of optically active serine and then reacting with a nucleophile or an electrophile, the above-described process (1) is not industrially advantageous. This is because the metal acetylide reagent should be used in large excess and only a poor yield can be achieved thereby. Moreover, it is needed in this process to synthesize the substrate in plural steps, which makes the performance troublesome.

Similarly, it is also needed to synthesize the substrate in plural steps in the processes (2) to (5), which makes the performance troublesome. To maintain the optical purity of a product at a high level, it is further needed to carry out the reaction at a low temperature with the use of a less basic organic copper reagent as the nucleophile and the occurrence of partial racemization is yet unavoidable. In these processes, furthermore, only an insufficient selectivity of functional groups is achieved and thus by-products having reacted with ester group are also formed.

As discussed above, these known processes each suffers from problems to be solved as an industrial process for producing optically active natural or unnatural amino acid derivatives. Therefore, it has been required to develop an industrially applicable process for producing optically active natural or unnatural amino acid derivatives without resort to any expensive reagents or troublesome procedures.

Concerning the process for producing aziridine-2-carboxylic acid as described above, the procedures and analytical methods are described in the document as cited above. When the inventors carried out a detailed follow-up experiment after establishing an appropriate analytical method, the yield reported in the document could be hardly achieved. It has been thus revealed that there is a serious problem in efficiently producing aziridine-2-carboxylic acid by this process on an industrial scale.

DISCLOSURE OF THE INVENTION

Under these circumstances, the inventors have conducted intensive studies on a process for efficiently producing optically active natural or unnatural amino acid derivatives starting with highly available optically active 3-haloalanine derivatives, in particular, optically active 3-chloroalanine derivatives. As a result, they have successfully found out that a natural or unnatural amino acid derivative can be very efficiently produced at a high optical purity by using an optically active 3-haloalanine derivative, in particular, an optically active 3-chloroalanine derivative via an optically active aziridine-2-carboxlic acid derivative protected at the amino group by a benzenesulfonyl group substituted by nitro at the 2- and/or 4-positions, or an optically active 3-haloalanine derivative protected at the amino group by a benzenesulfonyl group substituted by nitro at the 2- and/or 4-positions.

As the results of intensive studies on a process for efficiently producing optically active aziridine-2-carboxylic acid derivatives starting with optically active 3-haloalanine derivatives, in particular optically active 3-chloroalanine derivatives, they have further found out that an optically active aziridine-2-carboxylic acid derivative can be very efficiently produced by carrying out a reaction with the use of an optically active 3-haloalanine derivative, in particular an optically active chloroalanine derivative, under definite basic conditions.

Accordingly, the invention provides a process which comprises subjecting an optically active 3-haloalanine derivative represented by the following formula (1):

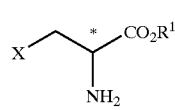

wherein X represents a halogen atom; $R^1$ represents a hydrogen atom or a monovalent organic group which is involved in a structure represented by $—CO_2R^1$ and thus is capable of serving as an ester type protective group of a carboxyl group; and * represents the position of an asymmetric carbon atom;

or its salt to an intramolecular cyclization reaction in the presence of a base followed by, if needed, ester hydrolysis to give an optically active aziridine-2-carboxylic acid derivative represented by the following formula (2):

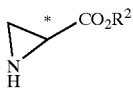

(2)

wherein * is as defined above; and $R^2$ has the same meaning as $R^1$ as defined above;

or its salt while maintaining the configuration at the 2-position, and then protecting the amino group followed by, if needed, ester hydrolysis to thereby give an optically active N-protected-aziridine-2-carboxylic acid represented by the following formula (3):

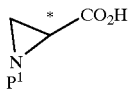

(3)

wherein * is as defined above; and $P^1$ represents a benzenesulfonyl group substituted by nitro at the 2- and/or 4-positions;

further treating it with an organic metal reagent represented by the following formula (5):

$$R^3 M \qquad (5)$$

wherein $R^3$ represents an optionally substituted cyclic or noncyclic alkyl group having 1 to 30 carbon atoms, an optionally substituted aralkyl group having 7 to 30 carbon atoms, an optionally substituted aryl group having 6 to 30 carbon atoms, an optionally substituted alkenyl group having 2 to 30 carbon atoms, or an optionally substituted alkynyl group having 2 to 30 carbon atoms; and M represents an atomic group containing an alkali metal atom or an alkaline earth metal atom or an atomic group containing a zinc ion;

followed by, if needed, deblocking to thereby give an optically active amino acid derivative represented by the following formula (6):

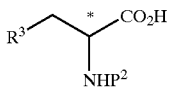

(6)

wherein $R^3$ and * are each as defined above; and $P^2$ has the same meaning as $P^1$ as described above or represents a hydrogen atom;

or its salt.

The invention further provides a process which comprises protecting the amino group of an optically active 3-haloalanine derivative represented by the above formula (1) or its salt followed by, if needed, ester hydrolysis to thereby give an optically active N-protected-3-haloalanine derivative represented by the following formula (4):

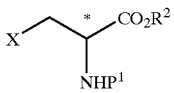

(4)

wherein X and * are each as defined above; $R^2$ has the same meaning as $R^1$ as defined above; and $P^1$ is the same as $P^1$ in the above formula (3);

or its salt, then subjecting it to an intramolecular cyclization reaction in the presence of a base followed by, if needed, ester hydrolysis to thereby give an optically active N-protected-aziridine-2-carboxylic acid represented by the above formula (3) or its salt, and further treating it with an organic metal reagent represented by the above formula (5) followed by, if needed, deblocking to thereby give an optically active amino acid derivative represented by the above formula (6) or its salt.

The invention furthermore provides a process which comprises protecting the amino group of an optically active 3-haloalanine derivative represented by the above formula (1) or its salt followed by, if needed, ester hydrolysis to thereby give an optically active N-protected-3-haloalanine derivative represented by the above formula (4) or its salt, then treating it with an organic metal reagent represented by the above formula (5) followed by, if needed, deblocking and/or ester hydrolysis to thereby an optically active amino acid derivative represented by the above formula (6) or its salt.

The invention furthermore provides a process for producing an optically active aziridine-2-carboxylic acid derivative represented by the above formula (2) or its salt by using an optically active 3-haloalanine derivative represented by the above formula (1) or its salt in the presence of a base, characterized by comprising using an alkali metal hydroxide or an alkaline earth metal hydroxide as the base, and carrying out an intramolecular cyclization reaction in the present of water at a temperature of 70° C. followed by, if needed, ester hydrolysis to thereby give an optically active aziridine-2-carboxylic acid derivative or its salt. The invention furthermore provides a process for producing an optically active aziridine-2-carboxylic acid derivative represented by the above formula (2) or its salt by using an optically active 3-haloalanine derivative represented by the above formula (1) or its salt in the presence of a base, characterized by comprising carrying out an intramolecular cyclization reaction by using an amine as the base followed by, if needed, ester hydrolysis to thereby give an optically active aziridine-2-carboxylic acid derivative or its salt.

The N-protected aziridine-2-carboxylic acids represented by the above formula (3) and salts thereof are novel compounds which have been proved as useful in producing optically active amino acid derivatives by the inventors. Accordingly, the invention further provides optically active-N-protected-aziridine-2-carboxylic acids represented by the following formula (3):

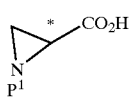

(3)

wherein $P^1$ represents a benzenesulfonyl group substituted by nitro at the 2- and/or 4-positions; and * represents the position of an asymmetric carbon atom;

and salts thereof.

By reacting an optically active N-protected aziridine-2-carboxylic acid represented by the above formula (3) or its salt with a metal acetylide represented by the following formula (8):

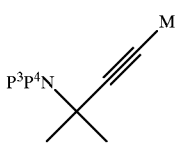

(8)

wherein M represents an atomic group containing an alkali metal or a halogenated alkali metal atom or an atomic group containing zinc halide; and $P^3$ and $P^4$ independently represent each a hydrogen atom or an amino-protective group, or $P^3$ and $P^4$ form together an amino-protective group;

an optically active amino acid derivative represented by the following formula (9):

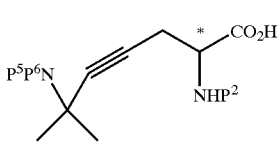

(9)

wherein $P^5$ and $P^6$ independently have the same meanings as $P^3$ and $P^4$ as described above; $P^3$ and $P^4$ independently represent each a hydrogen atom or an amino-protective group, or $P^3$ and $P^4$ form together an amino-protective group; and $P^2$ has the same meaning as $P^1$ as defined above or represents a hydrogen atom;

or its salt, which are novel compounds particularly useful in producing natural or unnatural amino acid derivatives, can be obtained. Namely, the invention furthermore provides optically active amino acid derivatives represented by the above formula (9) or salts thereof.

BEST MODE FOR CARRYING OUT THE INVENTION

Figure 1:
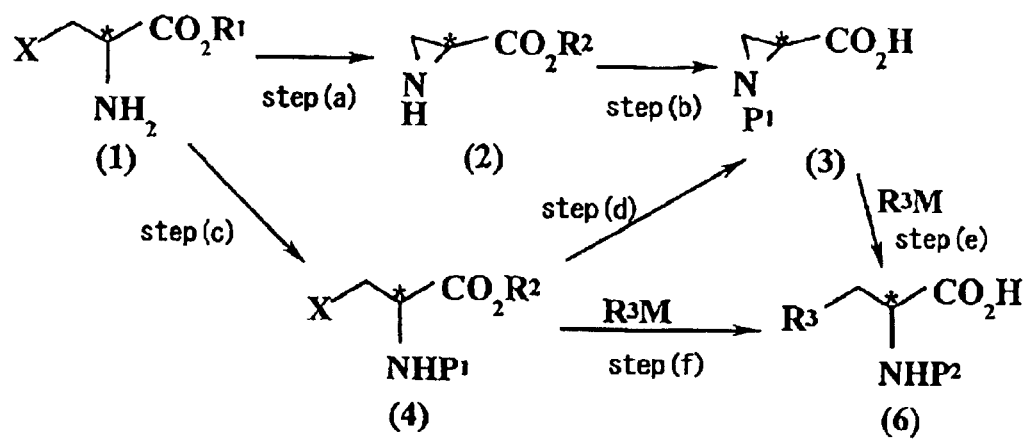
FIG. 1 is a scheme which roughly shows the process for producing optically active amino acid derivatives according to the invention.

Now, the invention will be described in detail. FIG. 1 schematically shows the invention.

First, the step (a) will be illustrated.

In this step, an optically active 3-haloalanine derivative represented by the formula (1) (also called the compound (1)) or its salt is subjected to intramolecular cyclization in the presence of a base followed by, if needed, ester hydrolysis to thereby give an optically active aziridine-2-carboxylic acid derivative represented by the formula (2) (also called the compound (2)) or its salt while maintaining the configuration at the 2-position.

In the above-described compound (1), X represents a halogen atom, for example, a fluorine, chlorine, bromine or iodine atom. It is preferable that X is a chlorine atom. $R^1$ represents a hydrogen atom or a monovalent organic group which is involved in a structure represented by $-CO_2R^1$ and thus can serve as an ester type protective group of a carboxyl group. The monovalent organic group as described above is not particularly restricted, so long as it has an effect of protecting carboxyl group. It may be selected from among, for example, those described in PROTECTIVE GROUPS IN ORGANIC SYNTHESIS 2nd Ed., John Wiley & Sons (1991), etc. Examples thereof include alkyl and aralkyl groups. In general, it is preferable to use a lower alkyl group, a benzyl group, etc. It is particularly preferable to use a lower alkyl group having 1 to 4 carbon atoms such as methyl, ethyl, n-propyl or isopropyl group. Among all, methyl and ethyl groups are preferable and methyl group is particularly preferable therefor.

Accordingly, examples of the compound (1) include various optically active 3-haloalanine esters, for example, optically active 3-haloalanines such as L-3-chloroalanine, D-3-chloroalanine, L-3-bromoalanine, D-3-bromoalanine, L-3-iodoalanine and D-3-iodoalanine, lower alkyl esters thereof having 1 to 4 carbon atoms such as methyl esters, ethyl esters, n-propyl esters and isopropyl esters, aralkyl esters such as benzyl esters. Among all, it is preferable to use L-3-chloroalanine or esters thereof (for example, L-3-chloroalanine methyl ester), still preferably L-3-chloroalanine.

These compounds can be produced by various methods. For example, L-3-chloroalanine, which is a preferable compound, can be easily produced by chlorinating L-serine (WO99/33785). Alternatively, it can be obtained by converting L-serine into methyl ester and then chlorinating the ester followed by ester hydrolysis. L-3-Chloroalanine methyl ester, which is also a preferable compound, can be produced by chlorinating L-serine into L-3-chloroalanine and then converting it into methyl ester. Alternatively, it can be obtained by converting L-serine into methyl ester and then chlorinating the ester.

The salt of the compound (1) is not particularly restricted. In case where the compound (1) is an optically active 3-haloalanine, for example, use can be made of a salt of the compound (1) with an acid or a salt of the compound (1) with a base. In case where the compound (1) is an optically active 3-haloalanine ester (i.e., in case where $R^1$ in the formula (1) is a monovalent organic group capable of serving as an ester type protective group of a carboxyl group), use can be made of a salt of the compound (1) with an acid.

The salt of the compound (2) is not particularly restricted. In case where the compound (2) is an optically active aziridine-2-carboxylic acid (i.e., in case where $R^1$ in the formula (2) is a hydrogen atom), use can be made of a salt of the compound (2) with an acid or a salt of the compound (2) with a base. In case where the compound (2) is an optically active aziridine-2-carboxylic acid ester (i.e., in case where $R^2$ in the formula (2) is a monovalent organic group capable of serving as an ester type protective group of a carboxyl group), use can be made of a salt of the compound (2) with an acid.

Examples of the salts of the above-described compound (1) or (2) with an acid include inorganic acid salts such as hydrochloride and sulfate; and organic acid salts such as formate, acetate, citrate, maleate, chloroacetate, trichloroacetate, fluoroacetate, trifluoroacetate, methanesulfonate, benzenesulfonate and p-toluenesulfonate, though the invention is not restricted thereto. It is generally preferable to use an inorganic acid salt such as hydrochloride.

Examples of the salts of the above-described compound (1) or (2) with a base include alkali metal salts such as lithium salt, sodium salt and potassium salt; alkaline earth metal salts such as magnesium salt, calcium salt and barium salt; amine salts such as triethylamine salt, diisopropylethylamine salt, dicyclohexylamine salt, diisopropylamine salt, isopropylamine salt, pyridine salt and aniline salt; and ammonium salts such as unsubstituted ammonium salt, tetrabutylammonium salt, tetraethylammonium salt and tetramethylammonium salt, though the invention is not restricted thereto. It is generally preferable to use an alkali metal salt, an alkaline earth metal salt or an amine salt, still preferably an alkali metal salt such as lithium, sodium or potassium salt or an amine salt such as triethylamine, diisopropylethylamine, diisopropylamine or isopropylamine.

Unless otherwise noted, salts of the compounds which will be described hereinafter mean the same acid salts or base salts as those cited above.

The salt of the compound (2) may be either the same as the salt of the compound (1) or different. Since this reaction is carried out in the presence of a base and the compound (2) is liable to become unstable under acidic conditions, it is generally preferable that the compound (2) is in the form of a free compound or a salt with a base, rather than a salt with an acid as described above. Among all, an alkali metal salt, an alkaline earth metal salt or an amine salt are preferable. It is particularly preferable to use an alkali metal salt such as lithium, sodium or potassium salt, or an amine salt such as triethylamine, diisopropylethylamine, diisopropylamine or isopropylamine salt.

Needless to say, a desired salt may be separately formed by using an acid or a base after the completion of the reaction, or the reaction product may be converted into a desired salt or a free compound.

The term "free state" as used herein means that the corresponding compound is not bonded to any basic compound. Namely, in the free state, a cation such as a metal ion or an ammonium ion, which is present when the compound occurs as a salt with a base, is replaced by a hydrogen ion.

In this step, the cyclization is carried out in the presence of a base. The base is not particularly restricted. Examples thereof include alkali metal hydroxide such as lithium hydroxide, sodium hydroxide and potassium hydroxide; alkaline earth metal hydroxides such as magnesium hydroxide, calcium hydroxide and barium hydroxide; alkali metal carbonates such as lithium carbonate, sodium carbonate and potassium carbonate; alkali metal hydrides such as lithium hydride and sodium hydride; metal alkoxides such as lithium methoxide, sodium methoxide, potassium methoxide, lithium ethoxide, sodium ethoxide, potassium ethoxide and potassium tert-butoxide; organic lithiums such as n-butyl lithium; organic lithium amides such as lithium diisopropylamide; organic magnesium amides such as magnesium diisopropylamide; Grignard reagents such as n-butyl magnesium chloride and tert-butyl magnesium chloride; amines such as triethylamine, diisopropylamine, dicyclohexylamine, diisopropylamine, diethylamine, isopropylamine, n-butylamine, pyridine and aniline; and ammonium hydroxide salts such as ammonium hydroxide (or ammonia), tetrabutylammonium hydroxide, tetraethylammonium hydroxide and tetramethylammonium hydroxide. Among all, it is preferable to use an alkali metal hydroxide, an alkaline earth metal hydroxide or an amine. It is particularly preferable to use an alkali metal hydroxide such as lithium hydroxide, sodium hydroxide or potassium hydroxide, or an amine such as triethylamine, diisopropylethylamine, diisopropylamine or isopropylamine. An appropriate base can be selected depending on the reaction solvent as will be described hereinafter.

The amount of the base used varies depending on the state of the compound (1), i.e., a free compound or a salt as described above. In case where the compound (1) is in free state and $R^1$ in the formula (1) and $R^2$ in the formula (2) are both hydrogen atoms, it is generally preferable to use 2 equivalents or more of the base. In case where $R^1$ and $R^2$ are both monovalent organic groups capable of serving as an ester type protective group of a carboxyl group, it is generally preferable to use 1 equivalent or more of the base. In case where $R^1$ in the formula (1) is a monovalent organic groups capable of serving as an ester type protective group of a carboxyl group and $R^2$ in the formula (2) is a hydrogen atom, it is generally preferable to use 2 equivalents or more of the base. Taking economy and convenience in reusing in the subsequent reaction, the upper limit of the amount of the base is generally 10 equivalents or less, preferably 5 equivalents or less. In case of performing ester hydrolysis simultaneously with the intramolecular cyclization reaction, it is adequate, needless to say, to use 1 equivalent or more of the base since the carboxyl group thus formed consumes 1 equivalent of the base.

Now, the amount of the base to be used will be described in greater detail. In case of using a free 3-haloalanine, for example, 2 equivalents or more of the base is generally used. In case of using a 3-haloalanine hydrochloride, 3 equivalents or more of the base is generally used. In case of using a 3-haloalanine lithium salt, 1 equivalent or more of the base is generally used. In case of performing the intramolecular cyclization reaction with the use of a free 3-haloalanine methyl ester, 1 equivalent or more of the base is generally used. In case of performing the intramolecular cyclization reaction with the use of a 3-haloalanine methyl ester hydrochloride, 2 equivalents or more of the base is generally used. In case where ester hydrolysis is also carried out in this reaction to thereby give a compound (2) of the formula (2) wherein $R^2$ is a hydrogen atom, 2 equivalents or more (for example, in case of using a free 3-haloalanine methyl ester) or 3 equivalents or more (for example, in case of using a 3-haloalanine methyl ester hydrochloride) of the base is generally used.

The reaction is usually carried out in a solvent, for example, water, an organic solvent or a mixture of water with an organic solvent. Examples thereof include alcohols such as methanol, ethanol and isopropanol; nitrites such as acetonitrile and ketones such as acetone and methyl ethyl ketone; ethers such as tetrahydrofuran, 1,2-dimethoxyethane, 1,4-dioxane and tert-butyl methyl ether; aromatic hydrocarbons such as toluene; halogenated hydrocarbons such as methylene chloride; and polar aprotic solvents such as N,N-dimethylformamide and N-methyl-2-pyrrolidone, though the invention is not restricted thereto. Among all, it is preferable to carry out this reaction in the presence of water. Therefore, it is preferable to carry out the reaction in water or a solvent mixture of water with an organic solvent, in particular, in water or a solvent mixture of water with an organic solvent compatible with water.

The reaction temperature is generally 0° C. or higher, usually 20° C. or higher from the viewpoint of reaction speed. The upper limit of the reaction temperature is the boiling point of the solvent in the reaction system employed.

The reaction can be completed within 24 hours, preferably 10 hours and still preferably 5 hours, after the completion of mixing.

Although the above-described compound (2) formed by this reaction under basic conditions is stable, olefin compounds or analogs or homologs thereof are liable to be formed by the liberation of hydrogen halide from the above-described compound (1) in the course of the formation of the above-described compound (2). To achieve the highest yield of the compound (2) or its salt by minimizing the formation of these by-products, the reaction should be carried out under restricted reaction conditions. The following 2 methods are particularly adequate therefor.

Method 1: In one method, the reaction is carried out by using an alkali metal hydroxide or an alkaline earth metal hydroxide as the base in the presence of water at 70° C. or higher. Examples of the base usable in this method include lithium hydroxide, sodium hydroxide, potassium hydroxide, magnesium hydroxide and calcium hydroxide. Among all, alkali metal hydroxides such as lithium hydroxide, sodium hydroxide and potassium hydroxide are suitable therefor.

Such a metal hydroxide may be formed by contacting another base, etc. with water. Although the reaction is preferably carried out in an aqueous solution, it is needless to say that the aqueous solution may further contain an organic solvent so long as no undesirable effect is exerted thereby. The concentration of the compound (1) in the solvent at the reaction is usually 10 W/V % or less, preferably 7.5 W/V % or less and still preferably 5 W/V % or less. The reaction temperature is usually 70° C. or higher, preferably 80° C. or higher and still preferably 90° C. or higher. The upper limit of the reaction temperature is the boiling point of the solvent in the reaction system employed.

In this method, it is preferable that the compound (1) or its salt is quickly exposed to the basic conditions as described above appropriate for the intramolecular cyclization reaction. Since it takes a certain period of time for the procedure on an industrial scale, it is preferable that the above-described compound (1) or its salt is added to the aqueous solution of the above-described base. In the most favorable and convenient embodiment, therefore, the above-described compound (1) or its salt is added to the aqueous solution of the above-described base which is maintained at a preferable temperature as specified above. In this case, it is preferable that the base is added all at once. Alternatively, it is possible, if needed, to add the base in portions or continuously. In such a case, it is recommended to maintain the ratio of the compound (1) to the base at the preferable level as described above. The reaction can be smoothly proceeded by using the alkali metal hydroxide in an amount of 2 equivalents or more but less than 4 equivalents, preferably from 2 to 3 equivalents, based on the above-described compound (1) in free state wherein $R^1$ is a hydrogen atom.

A lower concentration of the compound (1) is the more desirable in the reaction, as described above. However, the concentration of the compound (2) or its salt at the completion of the reaction is not restricted thereby. After the completion of the reaction, the concentration of the compound (2) or its salt can be further elevated by adding, if needed, the compound (1) or its salt to the reaction mixture and repeating the reaction.

Method 2: In the other method, the above-described amine is used as the base. Preferable examples of the amine include tertiary amines such as triethylamine and isopropylamine; secondary amines such as diisopropylamine and dicyclohexylamine; and primary amines such as isopropylamine and butylamine, and aliphatic amines are favorable in general, though the invention is not restricted thereto. Use of such an amine largely contributes to the minimization of the formation of by-products. In this case, the above-described amine may be contacted with the above-described compound (1) or its salt by an arbitrary method without restriction. Needless to say, the above-described amine may be added either in portions or continuously. As described above, the reaction is carried out in water or a solvent mixture of water with an organic solvent, preferably a solvent mixture of water with an organic solvent compatible with water. The reaction temperature is usually 20° C. or higher, preferably 30° C. or higher and still preferably 40° C. or higher. The upper limit of the reaction temperature is the boiling point of the solvent in the reaction system employed. In general, the reaction can be adequately carried out at a temperature around 50° C. Although the reaction concentration is not particularly restricted, the compound (1) in the solvent (preferably water) is usually 50 W/V % or less, preferably 30 W/V % or less and still preferably 20 W/V % or less. In general, the reaction can be carried out at a concentration of from 1 to 30 W/V %, preferably from 3 to 20 W/V %.

The above-described method 1 can be adequately employed as a process for producing an optically active aziridine-2-c-carboxylic acid or its salt by the intramolecular cyclization of an optically active 3-haloalanine or its salt, or a process for producing an optically active aziridine-2-carboxylic acid or its salt by the intramolecular cyclization and ester hydrolysis of an optically active 3-haloalanine ester or its salt. In particular, it has been employed as a process for producing an optically active aziridine-2-carboxylic acid or its salt by the intramolecular cyclization of an optically active 3-haloalanine or its salt.

The above-described method 2 is adequately usable as a process for producing an optically active aziridine-2-carboxylic acid or its salt by the intramolecular cyclization of an optically active 3-haloalanine or its salt.

According to the above-described methods 1 and 2, the above-described compound (2) or its salt can be produced at a high yield. In particular, the method 2 is preferable from the viewpoint that this method is superior in the flexibility in procedure, easiness in operation and prevention of misoperation on an industrial scale and enables the production of the above-described compound (2) at an extremely high yield.

Needless to say, the optically active aziridine-2-carboxylic acid esters or salts thereof obtained by the above-described methods can be individually introduced into optically active aziridine-2-carboxylic acids or salts thereof by a conventional method, for example, ester hydrolysis under basic conditions.

The compound (2) or its salt obtained by the above-described methods may be employed in the subsequent step as such, i.e., being as a liquid reaction mixture. Alternatively, it may be isolated by crystallization and then employed in the subsequent step.

In particular, the optically active aziridine-2-carboxylic acid (i.e., the compound (2) represented by the formula (2) wherein $R^2$ is a hydrogen atom) may be adequately isolated and purified by crystallizing, as the lithium salt, from a solvent mixture of water with an organic solvent compatible with water (i.e., a solvent mixture composed of water as a rich solvent and a water-compatible organic solvent as a poor solvent). In this case, it is preferable that, for example, a basic lithium compound such as lithium hydroxide is used as the base in the above-described method 1 and, after the reaction, the lithium salt is crystallized by using water as a rich solvent and a water-compatible organic solvent as a poor solvent. It is also preferable that, in the above-described method 2, a basic lithium compound such as lithium hydroxide is added after the reaction to form a lithium salt, and after washing the free amine with an organic solvent having no compatibility with water, if needed, the lithium salt is crystallized by using water as a rich solvent and a water-compatible organic solvent as a poor solvent.

Examples of the above-described basic lithium compound include lithium hydroxide, lithium carbonate, lithium methoxide, lithium ethoxide and lithium hydride. It is favorable to use lithium hydroxide therefor from the viewpoints of easiness in handling, cost, etc.

Particular examples of the above-described organic solvent compatible with water include 1,2-dimethoxyethane, 1,4-dioxane, tetrahydrofuran, diethylene glycol dimethyl ether, triethylene glycol dimethyl ether, polyethylene glycol dimethyl ether, acetonitrile, methanol, ethanol, n-propanol, isopropanol, t-butanol and acetone, though the invention is not restricted thereto. Among these solvents, methanol and ethanol are preferable and ethanol is still preferable.

Since the lithium salt of the above-described optically active aziridine-2-carboxylic acid (the compound (2) represented by the formula (2) wherein $R^2$ is a hydrogen atom) is highly soluble in water, it is preferable to increase the crystallization yield by lessening the amount of coexisting water, regulating the volume ratio of the above-described water-compatible organic solvent to water to 1 or more, or maintaining the final cooling temperature preferably at 10° C. or lower, still preferably 0° C. or lower.

Prior to the crystallization, a pretreatment such as adsorption by active carbon, etc. or filtration of insoluble matters may be effected for the elimination of impurities or decoloration.

The above-described lithium salt thus crystallized is separated by using a common solid/liquid separation technique such as filtration or centrifugation and then dried, if needed, under atmospheric or reduced pressure (in vacuo).

Since the aziridine-2-carboxylic acid (the compound (2) represented by the formula (2) wherein $R^2$ is a hydrogen atom) is not always stable under acidic conditions, it is favorable to handle this compound under neutral or basic (preferably basic) conditions in the isolation or in the subsequent step.

Next, the step (b) will be illustrated.

In this step, the above-described compound (2) or its salt is reacted with an amino-protecting agent followed by, if needed, ester hydrolysis to thereby give an optically active N-protected-aziridine-2-carboxylic acid (also called the compound (3)) or its salt.

In the compound (3), $P^1$ represents a benzenesulfonyl group substituted by nitro at the 2- and/or 4-positions. Particular examples thereof include 2-nitrobenzenesulfonyl, 4-nitrobenzenesulfonyl and 2,4-dinitrobenzenesulfonyl groups. It is preferable to use a 2-nitrobenzenesulfonyl or 4-nitrobenzenesulfonyl group therefor.

The salt of the compound (3) is formed by using the same acids or bases as those cited above concerning the compounds (1) and (2). The salt of the compound (3) in this step may be either the same as the salt of the compound (2) or different therefrom. Examples of the salts of the compound (2) to be used in this step include salts with the bases as cited above. Preferable examples thereof include alkali metal salt such as lithium, sodium and potassium salts, and amine salts such as triethylamine, diisopropylethylamine, diisopropylamine and isopropylamine salts.

The amino-protecting agent to be used in this step may be an arbitrary one without restriction, so long as it can introduce a benzenesulfonyl group substituted by nitro at the 2- and/or 4-positions into the amino group. Preferable examples thereof include 2-nitrobenzenesulfonyl chloride, 4-nitrobenzenesulfonyl chloride and 2,4-dinitrobenzenesulfonyl chloride. It is still preferable to use 2-nitrobenzenesulfonyl chloride or 4-nitrobenzenesulfonyl chloride therefor.

The above-described protecting agent may be used in an amount of 1 equivalent or more to the compound (2). Considering the economics, etc., it is adequate to use about 1 equivalent of the protecting agent.

It is generally preferable to use the above-described protecting agent together with a base. As the base, use may be made of the same bases as those usable in the above step (a) without restriction. It is preferable to use an alkali metal hydroxide such as lithium hydroxide, sodium hydroxide or potassium hydroxide, or a tertiary amine such as triethylamine or diisopropylethylamine. In this case, it is generally preferable to carry out this reaction under weakly basic conditions. In case of using pH value as an indication, it is generally adequate to carry out the invention at pH 9 to 11.

The amount of the base required in the reaction varies depending on the state of the compound (2), i.e., a free compound or a salt as described above. In case where the compound (2) is in free state and $R^2$ in the formula (2) is a hydrogen atom, it is generally preferable to use 2 equivalents or more of the base. In case where $R^2$ is a monovalent organic group capable of serving as an ester type protective group of a carboxyl group, it is generally preferable to use 1 equivalent or more of the base. Although the upper limit of the amount of the base employed is not particularly restricted, it is generally 10 equivalents or less, preferably 5 equivalents or less, considering economy and convenience in reusing in the subsequent reaction. In case of performing ester hydrolysis simultaneously, it is adequate, needless to say, to use about 1 equivalent or more of the base since the carboxyl group thus formed consumes 1 equivalent of the base.

The reaction is usually carried out in a solvent, for example, water, an organic solvent or a mixture of water with an organic solvent. Examples of the organic solvent include alcohols such as methanol, ethanol and isopropanol; nitrites such as acetonitrile and ketones such as acetone and methyl ethyl ketone; ethers such as tetrahydrofuran, 1,2-dimethoxyethane, 1,4-dioxane and tert-butyl methyl ether; aromatic hydrocarbons such as toluene; halogenated hydrocarbons such as methylene chloride; and polar aprotic solvents such as N,N-dimethylformamide and N-methyl-2-pyrrolidone, though the invention is not restricted thereto.

This reaction can be adequately carried out in water or a solvent mixture of an organic solvent with water. It is convenient and advantageous to use the liquid reaction mixture of the compound (2) obtained in the step (a). The reaction can be particularly adequately carried out in a solvent mixture with the above-described organic solvent compatible with water and water, for example, a solvent mixture of acetone with water.

The reaction can be carried out generally at the solidification point of the reaction mixture to about 80° C. The lower limit of the reaction temperature is usually −20° C., while the upper limit thereof is usually 50° C. or below. From the viewpoint of elevating the yield, it is preferable that the upper limit is 20° C. or below, still preferably 10° C. or below and particularly preferably 0° C. or below.

After mixing the reactants, the reaction can be completed usually within 10 hours, preferably 5 hours and still preferably 3 hours.

In case where $R^2$ in the formula (2) is a monovalent organic group capable of serving as an ester type protective group of a carboxyl group, ester hydrolysis may be carried out simultaneously with the above-described reaction. Alternatively, the product obtained after the above-described reaction may be introduced into the compound (3) in a conventional manner, for example, by ester hydrolysis under basic conditions.

The compound (3) thus formed may be obtained as a salt as described above. Alternatively, it may be obtained as an organic solvent containing the free compound (3) by using an isolation (separation) procedure such as extraction, concentration or solvent-replacement with the use of an organic solvent such as ethyl acetate, toluene or tetrahydrofuran. From the viewpoint of safety, such an isolation (separation) procedure for isolating (separating) the above-described compound (3) is preferably carried out at 50° C. or below, still preferably 40° C. or below.

The above-described compounds (3) are novel compounds which have been proved as useful in producing optically active amino acid derivatives by the inventors.

Next, the step (c) will be illustrated.

In this step, the above-described compound (1) or its salt is reacted with an amino-protecting agent followed by, if needed, ester hydrolysis to thereby give an optically active N-protected-3-haloalanine derivative (also called the compound (4)) or its salt.

In the compound (4), X is as defined concerning the compound (1), $R^2$ is as defined concerning the compound (2), and $P^1$ is as defined concerning the compound (3).

The amino-protecting agent to be used in this step is the same as in the step (b). It is generally preferable to use the protecting agent together with a base. As the base, use can be made of the same ones as those employed in the step (b). Also, the above-described protecting agent and base are each employed in the same amount as in the step (b).

The reaction is usually carried out in a solvent, for example, water, an organic solvent or a mixture of water with an organic solvent. Examples of the organic solvent include alcohols such as methanol, ethanol and isopropanol; nitrites such as acetonitrile and ketones such as acetone and methyl ethyl ketone; ethers such as tetrahydrofuran, 1,2-dimethoxyethane, 1,4-dioxane and tert-butyl methyl ether; aromatic hydrocarbons such as toluene; halogenated hydrocarbons such as methylene chloride; and polar aprotic solvents such as N,N-dimethylformamide and N-methyl-2-pyrrolidone, though the invention is not restricted thereto.

The reaction can be carried out generally at the solidification point of the reaction mixture to about 80° C. The lower limit of the reaction temperature is usually −20° C., while the upper limit thereof is usually 50° C. or below. From the viewpoint of elevating the yield, it is preferable that the upper limit is 20° C. or below, still preferably 10° C. or below and particularly preferably 0° C. or below.

After mixing the reactants, the reaction can be completed usually within 10 hours, preferably 5 hours and still preferably 3 hours.

In case where $R^1$ in the formula (1) is a monovalent organic group capable of serving as an ester type protective group of a carboxyl group, ester hydrolysis may be carried out simultaneously with the above-described reaction. Alternatively, the product obtained after the above-described reaction may be introduced into the compound (4) of the formula (4) wherein $R^2$ is a hydrogen atom in a conventional manner, for example, by ester hydrolysis under basic conditions.

The compound (4) thus formed may be obtained as a salt as described above. Alternatively, it may be obtained as an organic solvent containing the free compound (4) by extraction, concentration or solvent-replacement with the use of an organic solvent such as ethyl acetate, toluene or tetrahydrofuran.

Next, the step (d) will be illustrated.

In this step, the above-described compound (4) or its salt is subjected to intramolecular cyclization in the presence of a base followed by, if needed, ester hydrolysis to give the above-described compound (3) or its salt.

This reaction can be fundamentally carried out as in the step (a). Namely, the reaction conditions including base, reaction solvent, reaction temperature and reaction time are fundamentally the same as those employed in the step (a).

In case of the compound (4) where $R^2$ in the formula (4) is a monovalent organic group capable of serving as an ester type protective group of a carboxyl group, ester hydrolysis may be carried out simultaneously with the intramolecular cyclization reaction. Alternatively, the product obtained after the intramolecular cyclization reaction may be introduced into the compound (3) in a conventional manner, for example, by ester hydrolysis under basic conditions.

The compound (3) thus formed may be obtained as a salt as described above. Alternatively, it may be obtained as an organic solvent solution containing the free compound (3) by extraction, concentration or solvent-replacement with the use of an organic solvent such as ethyl acetate, toluene or tetrahydrofuran.

Next, the step (e) will be illustrated.

In this step, the above-described compound (3) or its salt is reacted with an organic metal reagent (5) (also called the compound (5)) represented by $R^3M$ to thereby give an optically active amino acid derivative represented by the formula (6) (also called the compound (6)) or its salt.

In the compound (5), $R^3$ represents an optionally substituted cyclic or noncyclic alkyl group having 1 to 30 carbon atoms, an optionally substituted aralkyl group having 7 to 30 carbon atoms, an optionally substituted aryl group having 6 to 30 carbon atoms, an optionally substituted alkenyl group having 2 to 30 carbon atoms, or an optionally substituted alkynyl group having 2 to 30 carbon atoms.

Examples of the optionally substituted cyclic or noncyclic alkyl group having 1 to 30 carbon atoms include methyl, ethyl, n-propyl, isopropyl, 2-(1,3-dioxolan-2-yl)ethyl, tert-butoxycarbonylmethyl, ethoxycarbonylmethyl, methoxycarbonylmethyl, cyclopropyl, cyclobutyl, cyclopentyl and cyclohexyl groups.

Examples of the optionally substituted aralkyl group having 7 to 30 carbon atoms include benzyl, p-methoxybenzyl, 3-phenylproypl and 2-phenylpropyl groups.

Examples of the optionally substituted aryl group having 6 to 30 carbon atoms include phenyl, p-chlorophenyl, p-fluorophenyl, p-methoxyphenyl and 2-naphthyl groups.

Examples of the optionally substituted alkenyl group having 2 to 30 carbon atoms include vinyl, allyl, crotyl, methallyl and benzylidene groups.

Examples of the optionally substituted alkynyl group having 2 to 30 carbon atoms include ethynyl, propynyl, 3,3-dimethyl-3-(N-benzyl)aminopropynyl, 3,3-dimethyl-3-aminopropynyl, 3,3-dimethyl-3-(N-benzyloxycarbonyl) aminopropynyl and 3,3-dimethyl-3-(N-tert-butoxycarbonylmethyl)aminopropynyl groups.

In the compound (5), M is not particularly restricted so long as it is a metal having a nucleophilic reactivity as the compound (5). Examples thereof include alkali metal atoms such as lithium, sodium and potassium; atomic groups containing an alkaline earth metal atom such as magnesium; and atomic groups containing a zinc atom. Among all, an atomic group containing an alkaline earth metal or an alkali metal atom is preferable therefor. Preferable examples of the atomic group containing an alkaline earth metal include atomic groups containing a magnesium atom such as MgCl and MgBr, and atomic groups containing a zinc atom such as ZnCl and ZnBr.

To prepare the compound (5), use can be made of various methods commonly known in the art depending on the type of the compound (5), for example, the methods described in Shin-Jikkengaku Koza (New Experimental Guidebook), vol. 12, Yuuki Kinzoku Kagaku (Organic Metal Chemistry), ed. by Nippon Kagaku-kai (Chemical Society of Japan). Examples thereof include a preparation process of deprotonating acidic proton by using a strong base, and a preparation process of reacting an organic halide with a metal atom.

Particular examples of the compound (5) which can be prepared by the process of deprotonating acidic proton by using a strong base include 3,3-dimethyl-3-(N-benzyl) aminopropynyl lithium, 3,3-dimethyl-3-(N,N-benzyl) aminopropynyl lithium, 3,3-dimethyl-3-aminopropynyl lithium, 3,3-dimethyl-3-(N-benzyloxycarbonyl) aminopropynyl lithium, 3,3-dimethyl-3-(N-tert-butoxycarbonylmethyl)aminopropynyl lithium, 3,3-dimethyl-3-(N-benzyl)aminopropynyl magnesium chloride, 3,3-dimethyl-3-(N,N-dibenzyl)aminopropynyl magnesium chloride, 3,3-dimethyl-3-aminopropynyl magnesium chloride, 3,3-dimethyl-3-(N-benzyloxycarbonyl) aminopropynyl magnesium chloride, 3,3-dimethyl-3-(N-tert-butoxycarbonylmethyl)aminopropynyl magnesium chloride, 3,3-dimethyl-3-(N-benzyl)aminopropynyl magnesium bromide, 3,3-dimethyl-3-(N,N-dibenzyl)

aminopropynyl magnesium bromide, 3,3-dimethyl-3-aminopropynyl magnesium bromide, 3,3-dimethyl-3-(N-benzyloxycarbonyl)aminopropynyl magnesium bromide and 3,3-dimethyl-3-(N-tert-butoxycarbonylmethyl) aminopropynyl magnesium bromide.

The above compound may be prepared by preliminarily reacting a compound having acidic proton with a strong base in the reaction with the compound (3) or its salt. Alternatively, it may be prepared in the course of the reaction by the same procedure.

Examples of the compound having acidic proton include 3,3-dimethyl-3-(N-benzyl)aminopropyne, 3,3-dimethyl-3-(N,N-dibenzyl)aminopropyne, 3,3-dimethyl-3-aminopropyne, 3,3-dimethyl-3-(N-benzyloxycarbonyl) aminopropyne and 3,3-dimethyl-3-(N-tert-butoxycarbonylmethyl)aminopropyne.

Examples of the strong base to be used in this case include organic lithium, organic lithium amides, Grignard reagents, organic magnesium amides, alkali metal hydrides and organic zinc. Examples of the organic lithium include n-butyl lithium, sec-butyl lithium and tert-butyl lithium. It is preferable to use n-butyl lithium. Examples of the organic lithium amides include diisopropyl lithium amide and lithium hexamethyldisilazide. Examples of the Grignard reagents include n-butyl magnesium chloride, n-butyl magnesium bromide, tert-butyl magnesium chloride and tert-butyl magnesium bromide. Examples of the organic magnesium amides include chloromagnesium diisopropylamide, chloromagnesium hexamethyldisilazide, bromomagnesium diisopropylamide and bromomagnesium hexamethyldisilazide. Examples of the alkali metal hydrides include lithium hydride, sodium hydride and potassium hydride. Among the above-described organic bases, it is particularly preferable to use organic lithium, organic lithium amides, Grignard reagents or organic magnesium amides.

Particular examples of the compound (5) which can be prepared by reacting an organic halide with a metal atom include Grignard reagents such as 2-(1,3-dioxolan-2-yl) ethyl magnesium chloride, 2-(1,3-dioxolan-2-yl)ethyl magnesium bromide, n-butyl magnesium chloride, benzyl magnesium chloride, n-butyl magnesium bromide and benzyl magnesium bromide, and Reformatsky reagents such as zinc bromide tert-butyl acetate.

Such a compound may be preliminarily prepared by reacting a corresponding organic halide with a metal prior to using. Alternatively, it may be prepared in the reaction system.

Examples of the organic halides include 2-(1,3-dioxolan-2-yl)ethyl chloride, 2-(1,3-dioxolan-2-yl)ethyl bromide, n-butyl chloride and tert-butyl acetate bromide. As the metal, use can be made of, for example, magnesium, zinc or lithium.

In this step, the compound (3) may be used either in the form of the above-described salt (for example, a salt with a base) or in free state (i.e., the compound (3) per se).

As the salt of the compound (3), it is preferable to use a metal salt of the compound (3), for example, an alkali metal salt such as lithium, sodium or potassium salt; or an alkaline earth metal salt such as magnesium salt. Preferable examples of the alkaline earth metal include MgCl, MgBr, etc. too.

In case where the compound (3) is in free state, it is preferable to preliminarily prepare a salt of the compound (3) with a base by using the base and then react the obtained salt with the organic metal compound represented by (5), or to prepare a salt of the compound (3) with a base in the reaction system while reacting with the compound (5), or to use the compound (5) in a larger amount without forming any salt separately and prepare a salt of the compound (3) with a base in the reaction system while reacting with the compound (5).

In case of using a base, the base is not particularly restricted. Examples thereof include alkali metal hydroxide such as lithium hydroxide, sodium hydroxide and potassium hydroxide; alkali metal carbonates such as lithium carbonate, sodium carbonate and potassium carbonate; alkaline earth metal hydroxides such as magnesium hydroxide; organic lithiums such as n-butyl lithium, sec-butyl lithium and tert-butyl lithium; organic lithium amides such as diisopropyl lithium amide and lithium hexamethyldisilazide; Grignard reagents such as n-butyl magnesium chloride, n-butyl magnesium bromide, tert-butyl magnesium chloride and tert-butyl magnesium bromide; organic magnesium amides such as chloromagnesium diisopropylamide, chloromagnesium hexamethyldisilazide, bromomagnesium diisopropylamide and bromomagnesium hexamethyldisilazide; and alkali metal hydrides such as lithium hydride, sodium hydride and potassium hydride.

In case of using the above-described base, the base is usually employed in an amount of 1 equivalent or more to the compound (3), preferably from 1 to 5 equivalents and still preferably from 1 to 3 equivalents.

The compound (5) is usually employed in an amount of 1 equivalent or more to the compound (3), preferably from 1 to 10 equivalents and still preferably from 1 to 5 equivalents. In case of using use the compound (5) in a larger amount without resort to any bases, the compound (5) is employed preferably in an amount of from 2 to 10 equivalents to the compound (3), still preferably from 2 to 5 equivalents.

In case of using the compound (3) as a metal salt as described above in this step, the compound (5) is usually employed in an amount of 1 equivalent or more to the compound (3), preferably from 1 to 10 equivalents and still preferably from 1 to 5 equivalents.

The reaction between the compound (3) or its salt with the compound (5) is usually carried out in an organic solvent, preferably an aprotic solvent. Various solvents may be used depending on the type of the compound (5). Examples thereof include ethers such as tetrahydrofuran, 1,4-dioxane, 1,2-dimethoxyethane, tert-butyl methyl ether and diisopropyl ether; aromatic hydrocarbons such as benzene and toluene; aliphatic hydrocarbons such as butane, pentane, hexane and heptane; halogenated hydrocarbons such as methylene chloride; and polar aprotic solvents such as N,N-dimethylformamide, N-methyl-2-pyrrolidone and dimethyl sulfoxide.

The reaction may be carried out by various methods commonly employed in reacting organic metals. For example, it may be carried out by mixing the compound (3) or its salt with the compound (5) in an amount as defined above in the above-described solvent at −78° C. to 150° C., preferably at −50° C. to 100° C. followed by stirring preferably for 0.01 to 50 hours, still preferably for 0.1 to 20 hours. In general, the reaction is carried out by adding the compound (3) or its salt to the solvent containing the compound (5).

After reacting the compound (3) or its salt with the compound (5), the amino group is deblocked, if needed. Thus the compound (6) of the formula (6) wherein $P^2$ is a hydrogen atom or its salt can be obtained. Namely, $P^2$ in the compound (6) is either the same as $P^1$ or a hydrogen atom. $R^3$ in the compound (6) is the same as $R^3$ in the compound (5). In case of $R^3$ in the compound (6) is an alkenyl group, compounds wherein $R^3$ is attached at a position different from the carbon atom to which M is attached are also involved in the scope of the compound (6).

After the completion of the reaction, the liquid reaction mixture may be used as such, if needed, and the compound (6) is deblocked to thereby give the compound (6) of the formula (6) wherein $P^2$ is a hydrogen atom. Alternatively, the following treatment may be carried out to isolate the compound (6) of the formula (6) wherein $P^2$ is a benzenesulfonyl group substituted by nitro at the 2- and/or 4-positions.

For example, the liquid reaction mixture is quenched by using water, a mineral acid, etc. and then treated by conventional procedures such as extraction, concentration and crystallization. Thus the compound (6) of the formula (6) wherein $P^2$ is a benzenesulfonyl group substituted by nitro at the 2- and/or 4-positions or its salt can be collected. As an adequate method, for example, the liquid reaction mixture is quenched by using water and a mineral acid and then the pH value is adjusted to the isoelectric point of the above-described compound (6). Thus the above-described compound (6) can be extracted as a free compound into an organic solvent such as ethyl acetate. Further, the extract may be subjected to crystallization by concentration, crystallization by cooling, crystallization by mixing with a poor solvent such as an aliphatic hydrocarbon, for example, hexane, heptane or methyl cyclohexane (these procedures may be combined together if needed) to thereby collect the above-described compound (6) as free crystals. Alternatively, the above-described compound (6) or its salt (preferably lithium salt) can be extracted by quenching the liquid reaction mixture with water and then extracting into an aqueous phase under basic conditions. It is also possible to crystallize the above-described salt by adding a water-compatible organic solvent to the extract.

In a still adequate method, for example, the liquid reaction mixture is quenched with water and the above-described compound (6) is extracted as its salt into an aqueous phase under basic conditions. Then this extract, i.e., an aqueous solution containing the salt of the above-described compound (6) is neutralized with an acid to thereby collect the above-described compound (6) as crystals in free state. In this case, it is preferable that the salt of the above-described compound (6) subjected to the neutralization crystallization is an alkali metal salt, still preferably lithium salt. As an acid, it is adequate to use an inorganic acid, preferably a hydrogen halide acid and still preferably hydrogen chloride (including hydrochloric acid). By neutralizing with the above-described acid, the lithium salt of the compound (6) is converted into a salt soluble in organic solvents and water (for example, a lithium halide such as lithium chloride) and the compound (6) in free state. Therefore, the above-described salt formed by the neutralization can be dissolved in a solvent mixture of water with a water-compatible organic solvent and the free compound (6) can be purified and isolated as crystals. From the viewpoints of elevating the yield and/or eliminating the coexisting organic impurities, it is preferable to carry out the crystallization in a solvent mixture of water with a water-compatible organic solvent.

Particular examples of the water-compatible organic solvent as described above include 1,2-dimethoxyethane, 1,4-dioxane, tetrahydrofuran, diethylene glycol dimethyl ether, triethylene glycol dimethyl ether, polyethylene glycol dimethyl ether, acetonitrile, methanol, ethanol, n-propanol, isopropanol, t-butanol and acetone, though the invention is not restricted thereto. Among these solvents, it is preferable to use acetone or a lower alcohol having 1 to 4 carbon atoms such as methanol or ethanol. Among all, it is preferable from the viewpoint of eliminating impurities to use a lower alcohol having 1 to 4 carbon atoms, still preferably methanol or ethanol and particularly preferably methanol.

To increase the crystallization yield of the above-described compound (6) or its salt, it is preferable to lessen the amount of water coexisting and maintain the final cooling temperature to 20° C. or lower, still preferably 10° C. or lower.

Prior to the crystallization, a pretreatment such as adsorption by active carbon, etc. or filtration of insoluble matters may be effected for the elimination of impurities or decoloration.

The crystals thus obtained may be separated by using a common solid/liquid separation technique such as filtration or centrifugation and then dried, if needed, under atmospheric or reduced pressure (in vacuo).

The excessive compound (5) can be converted into the compound of the formula (5) wherein M is a hydrogen atom, subjected to, if needed, extraction, washing, concentration, dehydration, etc. and then reused in the preparation of the compound (5).

The thus obtained compound (6) of the formula (6) wherein $P^2$ is a benzenesulfonyl group substituted by nitro at the 2- and/or 4-positions or its salt may be either employed in the subsequent step as carrying the protective group (i.e., the benzenesulfonyl group substituted by nitro at the 2- and/or 4-positions or deblocked. The deblocking may be carried out by an arbitrary method without restriction, so long as it is usable in deblocking the benzenesulfonyl group substituted by nitro at the 2- and/or 4-positions. For example, it can be carried out by using a thiol compound represented by the formula (7) (also called the thiol compound (7)).

In the thiol compound (7), $R^4$ represents an optionally substituted alkyl group having 1 to 30 carbon atoms, an optionally substituted aralkyl group having 7 to 30 carbon atoms or an optionally substituted aryl group having 6 to 30 carbon atoms. Examples of the optionally substituted alkyl group having 1 to 30 carbon atoms include methyl, ethyl, n-propyl, isopropyl and hexyl groups. Examples of the optionally substituted aralkyl group having 7 to 30 carbon atoms include benzyl, p-methoxybenzyl, 3-phenylpropyl and 2-phenylpropyl groups. Examples of the optionally substituted aryl group having 6 to 30 carbon atoms include phenyl, 4-tolyl, 3-tolyl, 2-tolyl, 4-chlorophenyl, 2-chlorophenyl, 4-fluorophenyl, 4-methoxyphenyl and 2-naphthyl groups. Particular examples of the above-described thiol compound include ethanethiol, 1-butanethiol, hexanethiol, thiophenol, 4-toluenethiol, 3-toluenethiol, 2-toluenethiol, 4-chlorobenzenethiol, 2-chlorobenzenethiol and mercaptoacetic acid. It is preferable to use thiophenol.

In the deblocking reaction with the use of the thiol compound (7), it is usually needed to use a base. Although the base is not particularly restricted, examples thereof include alkali metal carbonates such as lithium carbonate, sodium carbonate and potassium carbonate; alkali metal hydroxide such as lithium hydroxide, sodium hydroxide and potassium hydroxide; alkaline earth metal hydroxides such as magnesium hydroxide, calcium hydroxide and barium hydroxide; ammonium hydroxide salts such as tetraethylammonium hydroxide, tetrabutylammonium hydroxide and ammonium hydroxide; amines such as triethylamine, diisopropylamine and pyridine; and metal alkoxides such as lithium methoxide, sodium methoxide, potassium methoxide, lithium ethoxide, sodium ethoxide, potassium ethoxide and potassium tert-butoxide. Preferable examples thereof include alkali metal carbonates such as lithium carbonate, sodium carbonate and potassium carbonate; alkali metal hydroxide such as lithium hydroxide, sodium hydroxide and potassium hydroxide; and metal alkoxides such as lithium methoxide, sodium methoxide, potassium methoxide, lithium ethoxide, sodium ethoxide, potassium ethoxide and potassium tert-butoxide.

The reaction can be generally carried out in water, an organic solvent or a solvent mixture of water with an organic solvent. Although the organic solvent is not restricted, examples thereof include alcohols such as methanol, ethanol and isopropanol; nitriles such as acetonitrile and ketones such as acetone and methyl ethyl ketone; ethers such as tetrahydrofuran, 1,2-dimethoxyethane, 1,4-dioxane and tert-butyl methyl ether; aromatic hydrocarbons such as toluene;

halogenated hydrocarbons such as methylene chloride; and polar aprotic solvents such as N,N-dimethylformamide and N-methyl-2-pyrrolidone.

The reaction can be carried out by using, for example, from 1 to 20 equivalents, preferably from 1 to 5 equivalents to the compound (6), of the base and from 1 to 20 equivalents, preferably from 1 to 5 equivalents and still preferably from 1 to 3 equivalents to the compound (6), of the thiol compound (7) in the above-described solvent at a temperature of, for example, from 0° C. to the boiling point of the reaction system, preferably at 20° C. or higher and still preferably at 40° C. or higher.

As a result of further studies on adequate deblocking methods, the inventors have surprisingly found out that deblocking can be completed by using a metal alkoxide (still preferably an alkali metal alkoxide) such as sodium methoxide without resort to the above-described thiol compound (7). This novel deblocking reaction with the use of the metal alkoxide can be carried out without resort to the thiol compound which causes serious problems of bad smelling, etc., thereby very largely contributing to the production on an industrial scale from the viewpoints of improving the working environment, relieving the load in waste disposal, elevating the qualities of the product and the like.

In general, the deblocking reaction with the use of the metal alkoxide can be adequately performed in an organic solvent. As the organic solvent, use can be made of those employed in deblocking with the use of the thiol compound. It is particularly preferable to carry out this reaction in the coexistence of ethers such as tetrahydrofuran and 1,2-dimethoxyethane and/or alcohols such as methanol and ethanol.

The deblocking reaction with the use of the above-described metal alkoxide can be carried out usually by using the metal alkoxide in an amount of, for example, from 1 to 20 equivalents, preferably from 1 to 5 equivalents and still preferably from 1 to 3 equivalents to the compound (6) in an appropriate solvent as described above at a temperature of, for example, from 0° C. to the boiling point of the reaction mixture, preferably at 20° C. or higher and still preferably at 40° C. or higher.

The thus formed compound (6) of the formula (6) wherein $P^2$ is a hydrogen atom or its salt is generally highly soluble in water and, therefore, can be hardly extracted with an organic solvent. Thus, it is difficult to collect crystals of this compound. Although this compound may be obtained by using an ion exchange resin column, it is adequate to collect it in the form of crystals as described below.

After the completion of the deblocking reaction, the above-described base or metal alkoxide is neutralized by using, for example, hydrogen chloride or a hydrogen halide acid such as hydrochloric acid to thereby give a salt (for example, a lithium halide such as lithium chloride) soluble in organic solvents and water. In general, the above-described soluble salt thus formed by the neutralization is dissolved in a solvent mixture of water with a water-compatible organic solvent, i.e., using water as a rich solvent and a water-compatible organic solvent as a poor solvent. At the same time, the compound (6) of the formula (6) wherein $P^2$ is a hydrogen atom can be crystallized in free state or as a salt with an acid. In this case, the crystallization is preferably performed at around the isoelectric point of the above-described compound (6).

As the result of intensive studies to establish a more adequate crystallization method, the inventors have found out that it is preferable to crystallize the compound (6) of the formula (6) wherein $P^2$ is a hydrogen atom as an alkali metal salt such as lithium salt from an aqueous solution to thereby elevate the elimination ratio of impurities. Moreover, they have found out that it is particularly preferable to perform the crystallization by using an alkali metal halide salt (for example, a lithium halide such as lithium chloride) to thereby obtain the product with excellent qualities at a high yield. In this case, a water-compatible organic solvent may be also employed, if needed, to thereby elevate the yield or improve the qualities.

Particular examples of the water-compatible organic solvent include 1,2-dimethoxyethane, 1,4-dioxane, tetrahydrofuran, diethylene glycol dimethyl ether, triethylene glycol dimethyl ether, polyethylene glycol dimethyl ether, acetonitrile, methanol, ethanol, n-propanol, isopropanol, t-butanol and acetone, though the invention is not restricted thereto. Among all, it is preferable to use acetone or a lower alcohol having 1 to 4 carbon atoms and acetone is particularly preferable.

Since the compound (6) of the formula (6) wherein $P^2$ is a hydrogen atom or its salt (preferably a salt with an acid or a salt with a base) is highly soluble in water, it is preferable to elevate the crystallization yield by lessening the amount of water coexisting (usually 10 times by weight or less based on the compound (6), preferably 7 times by weight or less and still preferably 5 times by weight or less), elevating the volume ratio of the above-described water-compatible organic solvent to water (usually 1 or more, preferably 2 or more and still preferably 5 or more), maintaining the final cooling temperature to 20° C. or lower, still preferably 10° C. or lower, or separately adding a salt having an effect of salting out such as lithium chloride.

Prior to the crystallization, a pretreatment such as adsorption by active carbon, etc. or filtration of insoluble matters may be effected for the elimination of impurities or decoloration. It is also possible to wash an aqueous solution containing the compound (6) of the above-described formula (6) wherein $P^2$ is a hydrogen atom with an organic solvent such as toluene or ethyl acetate under acidic or basic conditions.

The crystals thus formed are separated by using a common solid/liquid separation technique such as filtration or centrifugation and then dried, if needed, under atmospheric or reduced pressure (in vacuo).

In case where a metal acetylide represented by the formula (8) (also called the metal acetylide (8)) is used as the compound (5) in this step, the thus formed optically active amino acid derivatives represented by the formula (9) are novel substances which are highly useful as an intermediate of drugs. Now, these compounds will be illustrated in greater detail.

In the metal acetylide (8), $P^3$ and $P^4$ independently represent each a hydrogen atom or an amino-protective group, or $P^3$ and $P^4$ form together an amino-protective group. The amino-protective group is not particularly restricted, so long as it is a protective group commonly used for protecting an amino group. For example, it may be selected from among those described PROTECTIVE GROUPS IN ORGANIC SYNTHESIS 2nd Ed., John Wiley & Sons (1991), etc.

Particular examples of $P^3$ and $P^4$ include a case where $P^3$ and $P^4$ are both benzyl groups, a case where $P^3$ and $P^4$ are both hydrogen atoms, a case where $P^3$ is a hydrogen atom and $P^4$ is a group selected from among, for example, benzyl, benzyloxycarbonyl, methoxycarbonyl, ethoxycarbonyl, allyloxycarbonyl, acetyl, benzoyl, chloroacetyl, p-toluenesulfonyl, benzenesulfonyl, 2-nitrobenzenesulfonyl, 4-nitrobenzenesulfonyl, tert-butoxycarbonylmethyl, ethoxycarbonylmethyl and methoxycarbonylmethyl groups, and a case where $P^3$ and $P^4$ form together a phthaloyl group. Preferable examples thereof include a case $P^3$ is a hydrogen atom and $P^4$ is a benzyl or benzyloxycarbonyl group, a case where $P^3$ and $P^4$ are both benzyl groups and a case where $P^3$ and $P^4$ are both hydrogen atoms.

In the metal acetylide (8), M is the same as M in the compound (5) and preferably lithium or magnesium.

The metal acetylide (8) can be prepared by treating optionally protected 3,3-dimethylpropargylamine represented by the formula (10) (also called the compound (10)) with at least one member selected from among organic lithium, organic lithium amide, a Grignard reagent and organic magnesium amide. In the compound (10), $P^3$ and $P^4$ are the same as in the compound (8).

Examples of the organic lithium include n-butyl lithium, sec-butyl lithium and tert-butyl lithium. It is preferable to use n-butyl lithium. Examples of the organic lithium amides include diisopropyl lithium amide and lithium hexamethyldisilazide. Examples of the Grignard reagents include n-butyl magnesium chloride, n-butyl magnesium bromide, tert-butyl magnesium chloride and tert-butyl magnesium bromide. Examples of the organic magnesium amides include chloromagnesium diisopropylamide, chloromagnesium hexamethyldisilazide, bromomagnesium diisopropylamide and bromomagnesium hexamethyldisilazide.

In the compound (9), $P^2$ represents the above-described $P^1$ or a hydrogen atom.

The conditions for the reaction between the compound (3) or its salt and the compound (8) including solvent, the amount of reagent, reaction method and post treatment are the same as those described concerning the reaction between the compound (3) or its salt and the compound (5). After reacting the compound (3) or its salt with the compound (8) by the above-described method, the product may be deblocked, if needed, to thereby give the compound (9) of the formula (9) wherein $P^2$ is a hydrogen atom or its salt. The deblocking may be carried out in the same manner as in the case of the above-described compound (6) or its salt.

Next, the step (f) will be illustrated.

In this step, the above-described compound (4) or its salt is reacted with the compound (5) followed by, if needed, deblocking of the amino group and/or ester hydrolysis, thereby giving the compound (6) or its salt.

The same reaction method as in the step (e) can be used.

Namely, the compound (4) may be used either in the form of the above-described salt (for example, a salt with a base) or in free state (i.e., the compound (4) per se) in this step.

As the salt of the compound (4), a metal salt of the compound (4) is preferable. Examples thereof include alkali metal salts such as lithium, sodium and potassium salts; and alkaline earth metal salts such as magnesium salt. Examples of the alkaline earth metal include MgCl, MgBr, etc. too as described above.

In case where the compound (4) is in free state, it is preferable to preliminarily prepare a salt of the compound (4) with a base by using the base and then react the obtained salt with the compound (5), or to prepare a salt of the compound (3) with a base in the reaction system while reacting with the compound (5), or to use the compound (5) in a larger amount without using any base separately and prepare a salt of the compound (4) with a base in the reaction system while reacting with the compound (5).

Different from the step (e), the hydrogen atoms on the amino group (nitrogen atom) of the compound (4) consume the compound (5) and/or the base. It is therefore preferable to use the compound (5) and/or the base in an amount larger by at least 1 equivalent, to the compound (4), than the amount of the compound (5) and/or the base to the compound (3) employed in the step (e).

In this step, the compound (9) can be obtained by using the metal acetylide (8) as the compound (5). Details of the reaction in this case are fundamentally the same as those of the above-described reaction between the compound (3) and the compound (8) but using the compound (4) as a substitute for the compound (3) and controlling the amounts of the compound (5) and the base to larger by at least 1 equivalent. In case where $R^2$ in the formula (4) is involved in a structure represented by $—CO_2R^2$ and thus is capable of serving as an ester type protective group of carboxyl group, the compound (9) can be obtained by ester hydrolysis in a conventional manner, for example, under basic or acidic conditions.

By using the process according to the invention, natural or unnatural optically active amino acid derivatives, which are useful as intermediates of drugs and pesticides, physiologically active substances, etc., can be efficiently produced starting with L-chloroalanine or L-chloroalanine methyl ester easily obtained from L-serine. Moreover, it is possible to efficiently produce optically active N-protected aziridinecarboxylic acids and optically active aziridine-2-carboxylic acid derivatives.

EXAMPLES

Now, the invention will be described in greater detail by reference to the following Examples. However, it is to be understood that the invention is not construed as being limited thereto.

Example 1

Production of (S)-aziridine-2-carboxylic acid

A mixture of 32.4 g (243 mmol) of a 30 wt. % aqueous solution of sodium hydroxide with 268 mL of purified water was heated to 90° C. To the resulting solution, 15.0 g (121 mmol) of (S)-3-chloroalanine was added over 30 minutes. After stirring at 90° C. for 10 minutes, the mixture was cooled to give an internal temperature of about 25° C. This liquid reaction mixture contained 9.21 g (106 mmol) of (S)-aziridine-2-carboxylic acid (yield: 87%).

Example 2

Production of (S)-aziridine-2-carboxylic acid

To 20 mL of a 0.8095 N aqueous solution of sodium hydroxide heated to 90° C., 1.0 g (8.095 mmol) of (S)-3-chloroalanine was added. After stirring at 90° C. for 30 minutes, the mixture was cooled to give an internal temperature of about 25° C. This liquid reaction mixture contained 599 mg (6.881 mmol) of (S)-aziridine-2-carboxylic acid (yield: 85%).

Example 3

Production of (S)-aziridine-2-carboxylic acid

To 14.3 mL of a 0.8095 N aqueous solution of sodium hydroxide heated to 90° C., 1.0 g (8.095 mmol) of (S)-3-chloroalanine was added. After stirring at 90° C. for 30 minutes, the mixture was cooled to give an internal temperature of about 25° C. This liquid reaction mixture contained 578 mg (6.638 mmol) of (S)-aziridine-2-carboxylic acid (yield: 82%).

Example 4

Production of (S)-aziridine-2-carboxylic acid

To 10 mL of a 0.8095 N aqueous solution of sodium hydroxide heated to 90° C., 1.0 g (8.095 mmol) of (S)-3-chloroalanine was added. After stirring at 90° C. for 30 minutes, the mixture was cooled to give an internal temperature of about 25° C. This liquid reaction mixture contained 549 mg (6.881 mmol) of (S)-aziridine-2-carboxylic acid (yield: 78%).

Example 5

Production of (S)-aziridine-2-carboxylic acid

To 20 mL of a 0.8095 N aqueous solution of sodium hydroxide heated to 70° C., 1.0 g (8.095 mmol) of (S)-3-chloroalanine was added. After stirring at 90° C. for 30 minutes, the mixture was cooled to give an internal temperature of about 25° C. This liquid reaction mixture contained 571 mg (6.557 mmol) of (S)-aziridine-2-carboxylic acid (yield: 81%).

Example 6

Production of (S)-aziridine-2-carboxylic acid

A mixture of 472 mg (8.095 mmol) of magnesium hydroxide with 20 mL of purified water was heated to 90° C. To the resulting solution, 1.0 g (8.095 mmol) of (S)-3-chloroalanine was added at once. After stirring at 90° C. for 30 minutes, the mixture was cooled to give an internal temperature of about 25° C. This liquid reaction mixture contained 296 mg (3.400 mmol) of (S)-aziridine-2-carboxylic acid (yield: 42%).

Example 7

Production of (S)-aziridine-2-carboxylic acid

A mixture of 0.600 g (8.095 mmol) of calcium hydroxide with 20 mL of purified water was heated to 90° C. To the resulting solution, 1.0 g (8.095 mmol) of (S)-3-chloroalanine was added at once. After stirring at 90° C. for 30 minutes, the mixture was cooled to give an internal temperature of about 25° C. This liquid reaction mixture contained 336 mg (3.858 mmol) of (S)-aziridine-2-carboxylic acid (yield: 47%).

Example 8

Production of (S)-aziridine-2-carboxylic acid

To 20 mL of a 1.2143 N aqueous solution of sodium hydroxide heated to 90° C., 1.408 g (8.095 mmol) of (S)-3-chloroalanine methyl ester hydrochloride was added. After stirring at 90° C. for 10 minutes, the mixture was cooled to give an internal temperature of about 25° C. This liquid reaction mixture contained 268 mg (3.076 mmol) of (S)-aziridine-2-carboxylic acid (yield: 38%).

Example 9

Production of (S)-aziridine-2-carboxylic acid 15.0 g (121 mmol) of (S)-3-chloroalanine was mixed with 295 ml of purified water and then cooled to give an internal temperature of 10° C. Then 38.0 g (376 mmol) of triethylamine was added thereto over 1 hour and 30 minutes while maintaining the internal temperature at 10° C. After the completion of the addition, the resulting mixture was heated to an internal temperature of 50° C. at a rate of about 10° C./hr. After reacting at the internal temperature of 50° C. to make the residual ratio of (S)-3-chloroalanine of 1% or less (about 3 hours), the reaction mixture was cooled to give an internal temperature of 5° C. This liquid reaction mixture contained 10.01 g (115 mmol) of (S)-aziridine-2-carboxylic acid (yield: 95%).

Example 10

Production of (S)-aziridine-2-carboxylic acid

A mixture of 30 mL of purified water with 4.90 g (48.4 mmol) of triethylamine was heated to 50° C. To the resulting solution, 1.50 g (12.1 mmol) of (S)-3-chloroalanine was added over 30 minutes. After stirring at 50° C. for 3 hours, the mixture was cooled to give an internal temperature of 10° C. This liquid reaction mixture contained 1.00 g (11.5 mmol) of (S)-aziridine-2-carboxylic acid (yield: 95%).

Example 11

Production of (S)-aziridine-2-carboxylic acid

A mixture of 7.5 mL of purified water with 4.90 g (48.4 mmol) of triethylamine was heated to 50° C. To the resulting solution, 1.50 g (12.1 mmol) of (S)-3-chloroalanine was added at once. After stirring at 50° C. for 3 hours, the mixture was cooled to give an internal temperature of 10° C. This liquid reaction mixture contained 0.97 g (11.1 mmol) of (S)-aziridine-2-carboxylic acid (yield: 92%).

Example 12

Production of (S)-aziridine-2-carboxylic acid

A mixture of 30 mL of purified water with 2.45 g (24.2 mmol) of diisopropylamine was heated to 50° C. To the resulting solution, 1.50 g (12.1 mmol) of (S)-3-chloroalanine was added at once. After stirring at 50° C. for 3 hours, the mixture was cooled to give an internal temperature of 10° C. This liquid reaction mixture contained 0.906 g (10.41 mmol) of (S)-aziridine-2-carboxylic acid (yield: 86%).

Example 13

Production of (S)-aziridine-2-carboxylic acid

A mixture of 30 mL of purified water with 2.45 g (24.2 mmol) of isopropylamine was heated to 50° C. To the resulting solution, 1.50 g (12.1 mmol) of (S)-3-chloroalanine was added at once. After stirring at 50° C. for 3 hours, the mixture was cooled to give an internal temperature of 10° C. This liquid reaction mixture contained 1.001 g (11.50 mmol) of (S)-aziridine-2-carboxylic acid (yield: 95%).

Example 14

Production of (S)-N-2-nitrobenzenesulfonyl-aziridine-2-carboxylic acid 200 mg (1.62 mmol) of (S)-3-chloroalanine was dissolved in 4.0 mL of water. After adding 136 mg (3.24 mmol) of lithium hydroxide monohydrate, the resulting mixture was slowly heated to 50° C. and then stirred for 3 hours. The reaction container was ice-cooled and 6.4 mL of acetone, 431 mg (1.94 mmol) of 2-nitrobenzenesulfonyl chloride and 68 mg (1.62 mmol) of lithium hydroxide monohydrate were successively added thereto at an internal temperature of 5° C. After 1 hour, 30 mL of ethyl acetate was added. Further, 6 N hydrochloric acid was added to adjust to pH 2.0. Then the reaction mixture was divided into layers and the organic layer was collected. The aqueous layer was extracted with 50 mL portions of ethyl acetate twice to give an organic layer. The organic layers thus obtained were combined, washed successively with 50 mL of water and 50 mL of a saturated aqueous solution of sodium chloride, dried over anhydrous sodium sulfate and filtered. After distilling off the solvent under reduced pressure, 265 mg of (S)-N-2-nitrobenzenesulfonyl-aziridine-2-carboxylic acid was obtained. Yield: 60%.

$^1$H-NMR (400 MHz, CDCl$_3$) δ2.80 (d, J=4.4 Hz, 1H), 3.10 (d, J=7.3 Hz, 1H), 3.61 (dd, J=4.4, 7.3 Hz, 1H), 7.77–7.82 (m, 3H), 8.23–8.27 (m, 1H).

Example 15

Production of (S)-N-2-nitrobenzenesulfonyl-aziridine-2-carboxylic acid

The liquid reaction mixture containing 10.01 g (115 mmol) of (S)-aziridine-2-carboxylic acid obtained in Example 1 was cooled to 2° C. and 255 mL of acetone was added thereto at an internal temperature of 2 to 5° C. While maintaining this solution at an internal temperature of −5 to 0° C., a mixture of 26.9 g (121 mmol) of 2-nitrobenzenesulfonyl chloride with 67 mL of acetone was quickly added thereto. Then the reaction was continued as such for additional 2 hours. This liquid reaction mixture contained 29.7 g (109 mmol) of (S)-N-2-nitrobenzenesulfonyl-aziridine-2-carboxylic acid (yield: 95%).

To this liquid reaction mixture, 1.1 g of conc. hydrochloric acid was added at an internal temperature of 3° C., thereby adjusting to pH 7.0. Next, the mixture was washed with 270 mL portions of toluene 4 times at an internal temperature of 5° C. At an internal temperature of 5° C., 330 mL of ethyl acetate was added thereto and then 3.5 g of conc. hydrochloric acid was added, thereby adjusting to pH 3.5. At an internal temperature of 5° C., the liquid reaction mixture was divided into layers and the organic layer was collected. Further, the aqueous layer was extracted with 270 mL of ethyl acetate at an internal temperature of 5° C. The organic layers were combined and washed with 100 mL portions of a 10% aqueous solution of sodium chloride twice at an internal temperature of 5° C. The organic layer thus obtained was concentrated under reduced pressure until the concentration of (S)-N-2-nitrobenzenesulfonyl-aziridine-2-carboxylic acid attained 50 wt. % (internal temperature: 30° C. or lower). Further, 119 mL of THF and 174 mL of toluene were added thereto and the mixture was concentrated under reduced pressure (internal temperature: 30° C. or lower) until the concentration of (S)-N-2-nitrobenzenesulfonyl-aziridine-2-carboxylic acid attained 50 wt. %. The concentrate thus obtained showed an ethyl acetate content of less than 0.1 wt. % and a moisture content of less than 0.1 wt. % and contained 28.3 g (104 mmol) of (S)-N-2-nitrobenzenesulfonyl-aziridine-2-carboxylic acid (yield: 90%).

Example 16

Production of (S)-N-2-nitrobenzenesulfonyl-aziridine-2-carboxylic acid

The liquid reaction mixture containing 9.21 g (106 mmol) of (S)-aziridine-2-carboxylic acid obtained in Example 1 was cooled to 2° C. and 150 mL of acetone was added thereto at an internal temperature of 2 to 5° C. While maintaining this solution at an internal temperature of −6 to −2° C., a mixture of 26.9 g (121 mmol) of 2-nitrobenzenesulfonyl chloride with 50 mL of acetone was added thereto over 1 hour. Then the reaction was continued as such for additional 2 hours. During the reaction, a 30 wt. % aqueous solution of sodium hydroxide was added to maintain the reaction system at pH 10.0 to 10.5 The obtained liquid reaction mixture contained 26.9 g (99 mmol) of (S)-N-2-nitrobenzenesulfonyl-aziridine-2-carboxylic acid (yield: 93%).

Example 17

Production of (S)-2-(2-nitrobenzenesulfonamido)-6-dibenzylamino-6-methyl-4-heptic acid 3.50 q (12.6 mmol) of N,N-dibenzyl-1,1-dimethylpropargylamine was dissolved in 50 mL of tetrahydrofuran (hereinafter referred to simply as THF). Then 9.2 mL (1.54 M, 14.0 mmol) of an n-butyl lithium/hexane solution was dropped thereinto at −78° C. over 5 minutes. After stirring at 0° C. for 1 hour, a solution of 1.15 g (4.2 mmol) of (S)-N-2-nitrobenzenesulfonyl-aziridine-2-carboxylic acid synthesized in accordance with Example 14 in 10 mL of THF was added thereto at 0° C. After stirring at the same temperature for 2 hours, the reaction was ceased by adding a saturated aqueous solution of ammonium chloride. Then the mixture was adjusted to pH 1.5 with conc. hydrochloric acid and extracted with ethyl acetate repeatedly thrice. The organic layer was washed with a saturated aqueous solution of sodium chloride, dried over anhydrous sodium sulfate and filtered. After distilling off the solvent under reduced pressure, 4.3 g of (S)-2-(2-nitrobenzenesulfonamido)-6-dibenzylamino-6-methyl-4-heptic acid was obtained. HPLC analysis (YMC Proc18, $KH_2PO_4$, $H_3PO_4$ buffer (pH 2.5)/acetonitrile=4/6, 1.0 mL/min, retention time: 5.8 min). Purity:24%, yeild:47%.

$^1$H-NMR (400 MHz, $CDCl_3$) δ1.34 (s, 6H), 2.86 (dd, J=16.6, 4.8 Hz, 1H), 2.92 (dd, J=16.6, 4.8 Hz, 1H), 3.79 (s, 4H), 3.85–3.90 (m, 1H), 4.25–4.35 (m, 1H), 7.05–7.30 (m, 10H), 7.60–7.72 (m, 2H), 7.80–7.85 (m, 1H), 8.05–8.15 (m, 1H).

This product was treated with trimethylsilyl diazomethane and analyzed as a methyl ester by HPLC. As a result, it showed an optical purity of 98% ee (Chiralpak AS, manufactured by Daicel, hexane/isopropanol=9/1, flow rate: 1.5 mL/min, retention time of (R)-compound: 9.6 min, retention time of (S)-compound: 11.2 min).

Example 18

Production of (S)-2-(2-nitrobenzenesulfonamido)-6-dibenzylamino-6-methyl-4-heptic acid 10.1 g (38.2 mmol, 2.2 equivalents) of N,N-dibenzyl-1,1-dimethylpropargylamine was dissolved in 40 mL of THF. Then 25.5 mL (1.5 M, 38.3 mmol, 2.2 equivalents) of an n-butyl lithium/hexane solution was dropped thereinto at −10° C. over 10 minutes. Then the resulting mixture was stirred at −10° C. for 1 hour to thereby give an acetylide solution. Into another reaction container, 50 mL of a solution of 4.81 g (17.4 mmol) of (S)-N-2-nitrobenzenesulfonyl-aziridine-2-carboxylic acid in THF was introduced. Under cooling at −10° C., the acetylide solution prepared above was dropped thereinto over 10 minutes. After stirring for 3 hours, the reaction was ceased by adding 40 mL of 1 N hydrochloric acid. After distilling off the THF under reduced pressure, 100 mL of ethyl acetate was added to the residue. Then the mixture was adjusted to pH 2 with 3 N hydrochloric acid and then divided into an organic layer and an aqueous layer. The organic layer was collected. The aqueous layer was extracted with 100 mL portions of ethyl acetate twice to further give organic layers. The organic layers thus obtained were combined, washed with a saturated aqueous solution of sodium chloride, dried over anhydrous sodium sulfate and filtered. After distilling off the solvent under reduced pressure, 16.76 g of a crude product of (S)-2-(2-nitrobenzenesulfonamido)-6-dibenzylamino-6-methyl-4-heptic acid was obtained. HPLC analysis (YMC Proc18, $KH_2PO_4$, $H_3PO_4$ buffer (pH 2.5)/acetonitrile=4/6, 1.0 mL/min, retention time: 5.8 min). Purity:49%, yeild:88%.

Example 19

Production of (S)-2-(2-nitrobenzenesulfonamido)-6-benzylamino-6-methyl-4-heptic acid 89.7 g (517.7 mmol, 2.9 equivalents) of N-benzyl-1,1-dimethylpropargylamine was dissolved in 266 mL of THF.

Then 344 mL (1.5 M, 516 mmol, 2.9 equivalents) of an n-butyl lithium/hexane solution was dropped thereinto at −10° C. over 30 minutes. Then the resulting mixture was stirred at −10° C. for 1 hour to thereby give an acetylide solution. Into another reaction container, 1000 mL of a solution of 48.5 g (178.2 mmol) of (S)-N-2-nitrobenzenesulfonyl-aziridine-2-carboxylic acid synthesized in accordance with Example 14 in THF was introduced. Under cooling at −10° C., the acetylide solution prepared above was dropped thereinto over 30 minutes. After stirring for 3 hours, the reaction was ceased by adding 180 mL of 3 N hydrochloric acid. Then the mixture was divided into an organic layer and an aqueous layer. The organic layer was collected. The aqueous layer was extracted with 250 mL of ethyl acetate to further give an organic layer. The organic layers thus obtained were combined and concentrated under reduced pressure to thereby give 63.8 g of a crude product of (S)-2-(2-nitrobenzenesulfonamido)-6-benzylamino-6-methyl-4-heptic acid (purity: 60% determined by $^1$H-NMR).

$^1$H-NMR (400 MHz, $C_5D_5N$) δ1.50 (s, 6H), 3.27, 3.33 (dd, J=5.8, 16.6 Hz, 2H), 4.22 (dd, J=12.2, 12.2 Hz, 2H), 4.69–4.72 (m, 1H), 7.21–7.29 (m, 4H), 7.50–7.64 (m, 3H), 7.85 (d, J=7.8 Hz, 1H), 8.47 (d, J=5.37 Hz, 1H).

Example 20

Production of (S)-2-(2-nitrobenzenesulfonamido)-6-benzylamino-6-methyl-4-heptic acid 36.7 g of a toluene solution containing 11.03 g (63.7 mmol, 3.0 equivalents) of N-benzyl-1,1-dimethylpropargylamine was cooled to −5° C. and then 110 mL of THF was added thereto. To this solution, 27.2 g (63.7 mmol, 3.0 equivalents) of a 15% n-butyl lithium/hexane solution was dropped over 2.5 hours at an internal temperature of −5° C. Then the resulting mixture was stirred for additional 3 hours to thereby give an acetylide solution. Into this solution, a concentrate containing (S)-N-2-nitrobenzenesulfonyl-aziridine-2-carboxylic acid obtained in Example 15 (corresponding to 5.78 g (21.2 mmol) of (S)-N-2-nitrobenzenesulfonyl-aziridine-2-carboxylic acid) was dropped over 3.5 hours under vigorously stirring at an internal temperature −5° C. Then the mixture was vigorously stirring for additional 5 hours to thereby complete the reaction. This liquid reaction mixture contained 7.56 g (17.0 mmol) of (S)-2-(2-nitrobenzenesulfonamido)-6-benzylamino-6-methyl-4-heptic acid (yield: 80%).

This liquid reaction mixture was dropped into 53 mL of purified water over 1 hour at an internal temperature of 2 to 5° C. After dividing, the aqueous layer was collected and washed with 53 mL portions of toluene 4 times. To the aqueous layer after washing, 33 mL of methanol was added and the mixture was heated to give an internal temperature of 20° C. After adjusting to pH 7 by adding conc. hydrochloric acid over 1 hour at an internal temperature of 20 to 30° C., the crystals thus precipitated were collected by filtration and washed with a mixture of 13 mL of purified water with 6 mL of methanol (5° C.). The moist crystals were vacuum dried (full vacuum, 40° C. or lower) to give 7.17 g (16.1 mmol) of (S)-2-(2-nitrobenzenesulfonylamido)-6-benzylamino-6-methyl-4-heptic acid (yield: 76%).

Example 21

Production of (S)-2-(2-nitrobenzenesulfonylamido)-6-benzyloxycarbonylamino-6-methyl-4-heptic acid Under an argon gas stream at 0° C., diisopropylamine (1.83 ml, 10.5 mmol) and n-butyl lithium (1.49 M, 6.9 ml of hexane solution, 10.29 mmol) were dropped in this order into dry THF (5 ml) and the resulting mixture was stirred at 0° C. for 30 minutes. After cooling the obtained solution to −78° C., a solution of N-benzyloxycarbonyl-1,1-dimethylpropargylamine (1.14 g, 5.25 mmol) in dry THF (5 ml) was dropped thereinto over 5 minutes. The reaction solution was stirred at −78° C. for 10 minutes and then at −10° C. for 10 minutes. Next, a solution of (S)-N-2-nitrobenzenesulfonyl-aziridine-2-carboxylic acid (580 mg, 2.10 mmol) in dry THF (5 ml) was dropped thereinto. After stirring at −10° C. for 2 hours and 30 minutes, the reaction was ceased by adding 5 ml of water to the reaction mixture. After adding 50 ml of ethyl acetate, 6 N hydrochloric acid was further added under vigorously stirring to adjust the mixture to pH 2.0. Thus, acidic components were migrated into the organic layer. The organic layer thus obtained were washed successively with water and a saturated aqueous solution of sodium chloride and dried over sodium sulfate. The organic layer was concentrated under reduced pressure and the crude product thus obtained was purified by silica gel column chromatography (Wako Gel C-200, 60 g, hexane: ethyl acetate=1:1). Thus 683 mg of (S)-2-(2-nitrobenzenesulfonylamido)-6-benzyloxycarbonylamino-6-methyl-4-heptic acid was obtained as a slightly brown oily substance (yield: 66%).

$^1$H-NMR (400 MHz, $CDCl_3$) δ1.47 (6H, s), 2.70 (2H, m), 4.28 (1H, brs), 5.08 (2H, s), 7.32 (5H, m), 7.79 (3H, m), 8.13 (1H, m).

Example 22

Production of (S)-2-amino-6-dibenzylamino-6-methyl-4-heptic acid hydrochloride 4.3 g (purity 24%, 2.0 mmol) of (S)-2-(2-nitrobenzenesulfonamido)-6-dibenzylamino-6-methyl-4-heptic acid obtained in Example 17 was dissolved in 80 mL of acetonitrile. Next, 1.4 g (10.1 mmol) of potassium carbonate and 0.86 mL (8.4 mmol) of thiophenol were successively added at room temperature. After reacting at 40° C. overnight, 0.7 g (5.1 mmol) of potassium carbonate and 0.4 mL (4.0 mmol) of thiophenol were successively added again at room temperature. Then the obtained mixture was further reacted at room temperature overnight. After distilling off the solvent, water was added to the residue. Then the resulting mixture was adjusted to pH 1.5 with conc. hydrochloric acid and the aqueous layer was washed with ethyl acetate thrice. The aqueous layer was concentrated and methanol was added. After filtering off the insoluble matters, the obtained filtrate was concentrated to thereby give 1.54 g of (S)-2-amino-6-dibenzylamino-6-methyl-4-heptic acid hydrochloride.

Example 23

Production of (S)-2-amino-6-benzylamino-6-methyl-4-heptic acid 63.8 g (purity 60%, 78.7 mmol) of the crude (S)-2-(2-nitrobenzenesulfonamido)-6-benzylamino-6-methyl-4-heptic acid obtained in Example 19 was dissolved in 1000 mL of methanol and 100 mL of THF. Next, 49.2 g (356.0 mmol) of potassium carbonate and 60.0 mL (534 mmol) of thiophenol were successively added at room temperature. After reacting at 40° C. for 24 hours, the methanol was distilled off under reduced pressure. Then 200 ml of ethyl acetate and 200 mL of water were added and the resulting mixture was divided into layers. The aqueous layer was further washed with 200 mL portions of ethyl acetate thrice. Then the aqueous layer was adjusted to pH 6 with conc. hydrochloric acid and washed with 200 mL portions of ethyl acetate thrice. The aqueous layer was concentrated to ⅓ and the inorganic salt thus precipitated was filtered and washed with methanol. The filtrate was combined with the aqueous layer and concentrated again under reduced pressure. Then acetone was added and the crystals thus formed were collected by filtration to give 17.5 g of (S)-2-amino-6-benzylamino-6-methyl-4-heptic acid (yield: 78.3%).

$^1$H-NMR (400 MHz, D$_2$O) δ1.57 (s, 6H), 2.82, 2.93 (dd, J=5.3, 17.6 Hz, 2H), 3.80 (t, J=5.3 Hz, 1H), 4.12 (s, 2H), 7.05–7.47 (m, 5H).

Example 24

Production of (S)-2-amino-6-benzylamino-6-methyl-4-heptic acid 7.17 g (16.1 mmol) of (S)-2-(2-nitrobenzenesulfonamido)-6-benzylamino-6-methyl-4-heptic acid obtained in Example 20 was added to 254 mL of purified water and 2.70 g (64.6 mmol) of lithium hydroxide monohydrate. Next, 2.68 g (24.2 mmol) of thiophenol was added. The resulting mixture was heated to 70° C. and reacted for 2 hours. Then the liquid reaction mixture was cooled to room temperature and washed with 44 mL portions of toluene thrice. To the aqueous layer thus obtained, 44 mL of ethyl acetate and 22 mL of methanol were successively added at an internal temperature of 3° C. Then the mixture was adjusted to pH 2 with conc. hydrochloric acid at an internal temperature of 5 to 10° C. The organic layer was collected and discarded. The remaining aqueous layer was washed with 44 mL portions of ethyl acetate thrice. To the aqueous layer thus obtained, a 4 N aqueous solution of lithium hydroxide was added slowly to adjust to pH 10.5. Subsequently, the mixture was concentrated under reduced pressure (internal temperature: 40° C. or lower) until the concentration of (S)-2-amino-6-benzylamino-6-methyl-4-heptic acid attained 21 wt. %. Next, 114 mL of acetone was added slowly at an internal temperature of 30° C. and then the mixture was cooled to give an internal temperature of 0° C. The crystals thus precipitated were collected by filtration and washed with 20 mL of acetone. Then the moist crystals thus obtained were vacuum-dried (full vacuum, 40° C. or lower) to give 3.95 g (15.2 mmol) of (S)-2-amino-6-benzylamino-6-methyl-4-heptic acid lithium salt (yield: 94%).

Example 25

Production of (S)-2-amino-6-benzylamino-6-methyl-4-heptic acid 7.19 g (16.1 mmol) of (S)-2-(2-nitrobenzenesulfonamido)-6-benzylamino-6-methyl-4-heptic acid obtained in Example 20 was added to 25.4 mL of purified water and 2.70 g (64.6 mmol) of lithium hydroxide monohydrate. Next, 3.57 g (32.2 mmol) of thiophenol was added. The resulting mixture was heated to 50° C. and reacted for 3 hours. Then the liquid reaction mixture was cooled to 10° C. or lower and 19 mL of methanol was added. Then it was adjusted to pH 7 with conc. hydrochloric acid at an internal temperature of 5 to 10° C. After adding 46 mL of ethyl acetate, the mixture was adjusted to pH 3.2 with conc. hydrochloric acid. The organic layer was collected and discarded. The remaining aqueous layer was washed with 46 mL portions of ethyl acetate thrice. To the aqueous layer thus obtained, 8.1 g of lithium chloride was added slowly while maintaining the internal temperature at 50° C. or lower. The insoluble matters thus formed were eliminated by filtration. The filtrate was vigorously stirred while maintaining the internal temperature at about 50° C. and then a 4 N aqueous solution of lithium hydroxide was slowly added thereto to adjust the mixture to pH 9.0. Next, the mixture was cooled to an internal temperature of 20° C. and stirred for 1 hour. The crystals thus precipitated were collected by filtration and washed with 17 mL of acetone. The moist crystals thus obtained were vacuum-dried (full vacuum, 40° C. or lower) to give 3.99 g (15.0 mmol) of (S)-2-amino-6-benzylamino-6-methyl-4-heptic acid lithium salt (yield: 93%).

Example 26

Production of (S)-2-amino-6-benzylamino-6-methyl-4-heptic acid 6.1 g of a toluene solution containing 1.83 g (10.6 mmol, 3.0 equivalents) of N-benzyl-1,1-dimethylpropargylamine was cooled to −5° C. and 18 mL of THF was added thereto. Into the resulting solution, a 15% n-butyl lithium/hexane solution was dropped over 2.5 hours while maintaining the internal temperature at −5° C. or lower. The mixture was further stirred for 3 hours to give an acetylide solution. Into this solution, a concentrate containing (S)-N-2-nitrobenzenesulfonyl-aziridine-2-carboxylic acid obtained in Example 15 (corresponding to 0.96 g (3.53 mmol) of S)-N-2-nitrobenzenesulfonyl-aziridine-2-carboxylic acid) was dropped over 3.5 hours under vigorously stirring at an internal temperature of −5° C. Then the reaction mixture was stirred for additional 5 hours to thereby complete the reaction. This liquid reaction mixture contained 1.26 g (2.8 mmol) of (S)-2-(2-nitrobenzenesulfonamido)-6-benzylamino-6-methyl-4-heptic acid (yield: 80%).

To this liquid reaction mixture, 1.62 g (8.4 mmol, 3 equivalents) of a solution of sodium methoxide in methanol (28 wt. % sodium methoxide) was added and the mixture was reacted under stirring at 60° C. for 23 hours. This solution contained 0.61 g (2.3 mmol) of (S)-2-amino-6-benzylamino-6-methyl-4-heptic acid (yield: 83%).

Example 27

Production of (S)-2-amino-6-benzylamino-6-methyl-4-heptic acid

To a solution of (S)-2-(2-nitrobenzenesulfonamido)-6-benzylamino-6-methyl-4-heptic acid (471.1 mg) in dry dimethoxyethane (7 ml), a 28% sodium methoxide/methanol solution (0.75 ml, 3.50 equivalents) was added under an argon atmosphere at room temperature. The resulting mixture was stirred at room temperature for 43 hours and thus it was confirmed that the starting materials disappeared. At room temperature, sulfuric acid (0.18 g) was added to the reaction mixture. After stirring for 10 minutes, the mixture was concentrated to dryness to give a foamy product (0.78 g). After adding ethyl acetate (20 ml) and ethanol (4 ml), the mixture was heated with a dryer. The insoluble matters were collected by filtration and washed with ethyl acetate (3 ml). The filtered solid matters were washed with methanol (9 ml) and the soluble fraction was collected. The ethyl acetate/ethanol filtrate was concentrated and, after adding ethyl acetate (10 ml) and water (3 ml), divided into layers. The organic layer was re-extracted with water (2 ml). The aqueous layer thus obtained was combined with the above-described methanol-soluble fraction and concentrated to dryness to give a foamy product (0.54 g). As shown below, this product was converted into methyl (S)-2-[N-(tert-butoxycarbonyl)amino]-6-(N-benzylamino)-6-methyl-4-heptate and the optical purity was analyzed. Into a solution of the above-described foamy product (0.54 g) in methanol (13 ml), thionly chloride (0.6 ml) was slowly dropped under ice-cooling. The resulting mixture was stirred overnight under ice-cooling to room temperature. Then, thionyl chloride (0.6 ml) and methanol (3 ml) were further added under ice-cooling. The resulting mixture was stirred under ice-cooling to room temperature for 1.5 hours and then under heating at 50° C. for additional 5 hours. Next, the reaction mixture was concentrated under reduced pressure and ethyl acetate (10 ml) and a saturated cold aqueous solution of sodium hydrogencarbonate (5 ml) were added to the concentrate. The obtained mixture was divided into layers and the aqueous layer was re-extracted with ethyl acetate (12 ml). The extract layer thus obtained was concentrated to about 5 ml and a solution of di-tert-butyl dicarbonate (0.3 g) in ethyl acetate (3 ml) was added thereto. After stirring at room temperature for 1.5 hours, citric acid (0.75 g) and cold water (15 ml) were successively added to the liquid reaction mixture. Thus the mixture was divided into layers and the organic layer was re-extracted with cold water (8 ml). Since the target compound still remained in the organic layer, the organic layer was re-extracted with cold water (10 ml) containing citric acid (0.42 g). Sodium carbonate (1.45 g) was added to the aqueous layer thus obtained and the mixture was extracted with ethyl acetate (25 ml, 22 ml) twice. After drying over sodium sulfate, filtering, concentrating and vacuum-drying, methyl (S)-2-[N-(tert-butoxycarbonyl)amino]-6-(N-benzylamino)-6-methyl-4-heptate (270 mg, overall yield: 68%) was obtained. As the result of high performance liquid chromatographic analysis with the use of an optically active column (Chiral Cell OD-H, manufactured by Daicel), this product had an optical purity of 96% ee.

$^1$H-NMR (400 MHz, CDCl$_3$) δ1.37 (s, 6H), 1.45 (s, 9H), 2.68–2.86 (m, 2H), 3.76 (s, 3H), 3.82 (s, 2H), 4.48 (m, 1H), 5.32 (br d, 1H), 7.21–7.40 (m, 5H).

Referential Example 1

Production of (S)-aziridine-2-carboxylic acid 1.02 g (8.256 mmol) of (S)-3-chloroalanine was mixed with 2.94 mL of purified water. Then 2.451 g of a 7.15 N aqueous solution of sodium hydroxide was dropped thereinto over 30 minutes at 25° C. and the resulting mixture was stirred at 25° C. for 24 hours. This liquid reaction mixture contained 206 mg (2.36 mmol) of (S)-aziridine-carboxylic acid (yield: 29%).

Referential Example 2

Production of (S)-aziridine-2-carboxylic acid 1.00 g (8.094 mmol) of (S)-3-chloroalanine was mixed with 4.20 ml of purified water. Then 2.60 g of a 6.306 N aqueous solution of potassium hydroxide was dropped thereinto over 15 minutes at 25° C. Then the resulting mixture was heated to 60° C. and stirred for 4 hours. Then, it was cooled to give an internal temperature of about 25° C. This liquid reaction mixture contained 91.6 mg (1.05 mmol) of (S)-aziridine-carboxylic acid (yield: 13%).

Referential Example 3

Production of (S)-aziridine-2-carboxylic acid

To 20 mL of a 0.8095 N aqueous solution of sodium hydroxide heated to 50° C., 1.0 g (8.095 mmol) of (S)-3-chloroalanine was added. After stirring at 50° C. for 1 hour, the mixture was cooled to give an internal temperature of about 25° C. This liquid reaction mixture contained 373 mg (4.290 mmol) of (S)-aziridine-carboxylic acid (yield: 53%).

Referential Example 4

Production of (S)-aziridine-2-carboxylic acid

To 20 mL of a 0.8095 N aqueous solution of sodium hydroxide adjusted to 25° C., 0.1 g (8.095 mmol) of (S)-3-chloroalanine was added. After stirring at 25° C. for 24 hours, the liquid reaction mixture contained 331 mg (3.800 mmol) of (S)-aziridine-carboxylic acid (yield: 47%).

Referential Example 5

Production of (S)-2-(p-toluenesulfonamido)-6-dibenzylamino-6-methyl-4-heptic acid 1.32 g (5.20 mmol, 10 equivalents) of N,N-dibenzyl-1,1-dimethylpropargylamine was dissolved in 20 mL of THF. Then 4.0 mL (1.5 M, 6.0 mmol, 12 equivalents) of an n-butyl lithium/hexane solution was dropped thereinto at −78° C. over 5 minutes. After stirring at 0° C. for 1 hour, a solution of 121.0 mg (0.50 mmol) of (S)-N-p-toluenesulfonyl-aziridine-2-carboxylic acid in 2 mL of THF was added thereto at 0° C. After stirring at the same temperature for 2 hours, the reaction was ceased by adding a saturated aqueous solution of ammonium chloride. Then the mixture was adjusted to pH 2 with conc. hydrochloric acid and divided into an organic layer and an aqueous layer. The organic layer was collected. The aqueous layer was extracted with 100 mL portions of ethyl acetate twice and the organic layer was collected. The obtained organic layers were combined, washed with a saturated aqueous solution of sodium chloride, dried over anhydrous sodium sulfate and filtered. After distilling off the solvent under reduced pressure, a crude product of (S)-2-(p-toluenesulfonamido)-6-dibenzylamino-6-methyl-4-heptic acid was obtained. The crude product thus obtained was analyzed by $^1$H-NMR and the purity thereof was determined based on the integral value (proton at the propagyl position (2.8–2.9 ppm) of (S)-2-(p-toluenesulfonamido)-6-dibenzylamino-6-methyl-4-heptic acid)). The yield calculated therefrom was 14%.

Industrial Applicability

Natural or unnatural optically active amino acid derivatives, which are useful as intermediates of drugs and pesticides, physiologically active substances, etc., can be efficiently produced starting with optically active 3-haloalanine derivatives, in particular, optically active 3-chloroalanine. Moreover, optically active N-protected-aziridine-2-carboxylic acids and optically active aziridine-2-carboxylic acid derivatives can be efficiently produced.

What is claimed is:

1. A process for producing an optically active amino acid derivative represented by the following formula (6):

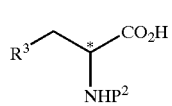

(6)

wherein $R^3$ represents an optionally substituted cyclic or noncyclic alkyl group having 1 to 30 carbon atoms, an optionally substituted aralkyl group having 7 to 30 carbon atoms, an optionally substituted aryl group having 6 to 30 carbon atoms, an optionally substituted alkenyl group having 2 to 30 carbon atoms, or an optionally substituted alkynyl group having 2 to 30 carbon atoms, $P^2$ represents a benzenesulfonyl group substituted by nitro at the 2- and/or 4-positions or hydrogen atom and * represents the position of an asymmetric carbon atom;

or its salt characterized by comprising treating an optically active N-protected aziridine-2-carboxylic acid represented by the following formula (3):

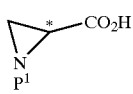 (3)

wherein $P^1$ represents a benzenesulfonyl group substituted by nitro at the 2- and/or 4- positions and * is as defined above, or its salt with an organic metal reagent represented by the following formula (5):

$R^3M$ (5)

wherein $R^3$ is as defined above and M represents an atomic group containing an alkali metal atom or an alkaline earth metal atom or an atomic group containing a zinc ion; followed by, if needed, deblocking.

2. The production process as claimed in claim 1, wherein M in the formula (5) is lithium, sodium, MgCl, MgBr, ZnCl or ZnBr.

3. A production process as claimed in claim 1 or 2, wherein said deblocking is performed with the use of a thiol compound represented by the following formula (7):

$R^4SH$ (7)

wherein $R^4$ is as defined above;
to give a compound represented by the formula (6) wherein $P^2$ is a hydrogen atom.

4. The production process as claimed in claim 2, wherein said thiol compound represented by the formula (7) is thiophenol.

5. A production process as claimed in claim 1 or 2, wherein said deblocking is performed with the use of a metal alkoxide to give a compound represented by the formula (6) wherein $P^2$ is a hydrogen atom.

6. The production process as claimed in claim 5, wherein said metal alkoxide is an alkali metal alkoxide.

7. A production process as claimed in claim 1 or 2, wherein a metal acetylide represented by the following formula (8):

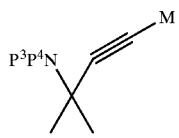 (8)

wherein M, $P^3$ and $P^4$ are each as defined above;
is used as said organic metal reagent represented by the formula (5) to give an optically active amino acid derivative represented by the following formula (9):

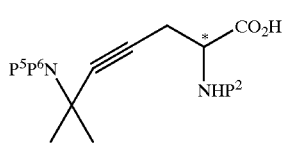 (9)

wherein $P^2$, $P^5$, $P^6$ and * are each as defined above;
or its salt as the compound represented by the formula (6).

8. The production process as claimed in claim 7, wherein said metal acetylide represented by the formula (8) is prepared by treating an optionally protected 3,3-dimethylpropargylamine represented by the following formula (10):

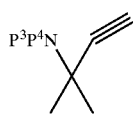 (10)

wherein $P^3$ and $P^4$ are each as defined above;
with at least one member selected from among organic lithium, organic lithium amide, a Grignard reagent and organic magnesium amide.

9. A production process as claimed in claim 7, wherein $P^3$ and $P^4$ in the formula (8) respectively represent a hydrogen atom and a benzyl group.

* * * * *